United States Patent [19]

Fang et al.

[11] Patent Number: 5,840,898
[45] Date of Patent: Nov. 24, 1998

[54] METHOD OF REMOVING HEAVY METAL CONTAMINANTS FROM ORGANIC COMPOUNDS

[75] Inventors: Francis Gerard Fang, Durham; Melissa Williams Lowery, Raleigh; Shiping Xie, Cary, all of N.C.

[73] Assignee: Glaxo Wellcome, Inc., Research Triangle Park, N.C.

[21] Appl. No.: 732,435

[22] PCT Filed: May 2, 1995

[86] PCT No.: PCT/US95/05425

§ 371 Date: Nov. 1, 1996

§ 102(e) Date: Nov. 1, 1996

[87] PCT Pub. No.: WO95/29917

PCT Pub. Date: Nov. 9, 1995

Related U.S. Application Data

[63] Continuation of Ser. No. 237,081, May 3, 1994, Pat. No. 5,491,237.

[51] Int. Cl.⁶ .............................................. C07D 491/147
[52] U.S. Cl. .................................. 546/41; 546/48; 423/22
[58] Field of Search ....................... 546/41, 48; 588/236; 423/22; 23/296, 297

[56] References Cited

U.S. PATENT DOCUMENTS

| | | | |
|---|---|---|---|
| 4,399,276 | 8/1983 | Miyasaka et al. | 546/48 |
| 4,399,282 | 8/1983 | Miyasaka et al. | 546/48 |
| 4,413,118 | 11/1983 | Roberts et al. | 536/7.1 |
| 4,473,692 | 9/1984 | Miyasaka et al. | 546/48 |
| 4,545,880 | 10/1985 | Miyasaka et al. | 204/158 |
| 4,778,891 | 10/1988 | Tagawa et al. | 546/18 |
| 4,871,855 | 10/1989 | Marko et al. | 546/134 |
| 4,894,456 | 1/1990 | Wall et al. | 546/41 |
| 4,943,579 | 7/1990 | Vishnuvajjala et al. | 514/283 |
| 4,965,364 | 10/1990 | Marko et al. | 546/134 |
| 4,981,968 | 1/1991 | Wall et al. | 546/48 |
| 5,049,668 | 9/1991 | Wall et al. | 540/41 |
| 5,053,512 | 10/1991 | Wani et al. | 546/48 |
| 5,106,742 | 4/1992 | Wall et al. | 435/233 |
| 5,122,526 | 6/1992 | Wall et al. | 514/253 |
| 5,122,606 | 6/1992 | Wani et al. | 546/41 |
| 5,126,494 | 6/1992 | Glheany et al. | 568/807 |
| 5,162,532 | 11/1992 | Comins et al. | 546/48 |
| 5,180,722 | 1/1993 | Wall et al. | 514/219 |
| 5,191,082 | 3/1993 | Comins et al. | 546/116 |
| 5,200,524 | 4/1993 | Comins et al. | 546/301 |
| 5,212,317 | 5/1993 | Comins et al. | 546/301 |
| 5,227,380 | 7/1993 | Wall et al. | 514/253 |
| 5,227,543 | 7/1993 | Sharpless et al. | 568/860 |
| 5,243,050 | 9/1993 | Comins et al. | 546/116 |
| 5,244,903 | 9/1993 | Wall et al. | 514/279 |
| 5,247,089 | 9/1993 | Comins et al. | 546/48 |
| 5,254,690 | 10/1993 | Comins et al. | 546/302 |
| 5,258,516 | 11/1993 | Comins et al. | 546/116 |
| 5,260,461 | 11/1993 | Hartung et al. | 549/447 |
| 5,264,579 | 11/1993 | Comins et al. | 546/301 |
| 5,315,007 | 5/1994 | Comins et al. | 546/116 |
| 5,321,140 | 6/1994 | Comins et al. | 546/298 |
| 5,342,947 | 8/1994 | Lackey et al. | 546/41 |

FOREIGN PATENT DOCUMENTS

| | | |
|---|---|---|
| 0 321 122 A2 | 6/1989 | European Pat. Off. |
| 0 325 247 A1 | 7/1989 | European Pat. Off. |
| 0 418 099 A2 | 3/1991 | European Pat. Off. |
| 429963 | 5/1991 | European Pat. Off. |
| 0 429 963 A | 6/1991 | European Pat. Off. |
| 0 540 099 A1 | 5/1993 | European Pat. Off. |
| 0 556 585 A2 | 8/1993 | European Pat. Off. |
| 152 774 | 12/1981 | Germany |
| 63-33355 | 2/1988 | Japan |
| 89/06225 | 7/1989 | WIPO |
| 91/05556 | 5/1991 | WIPO |
| 91/16322 | 10/1991 | WIPO |
| 9207856 | 5/1992 | WIPO |
| 92/11263 | 7/1992 | WIPO |
| 92/20677 | 11/1992 | WIPO |
| 93/07142 | 4/1993 | WIPO |
| 9316698 | 9/1993 | WIPO |
| 94/11377 | 11/1993 | WIPO |
| 93/25556 | 12/1993 | WIPO |
| 94/04160 | 3/1994 | WIPO |

OTHER PUBLICATIONS

Kirk–Othmer, Encyclopedia of Chem. Technology–4th Ed., vol. 7, pp. 683 and 721, 1993.

R.P. Herzberg, *Journal of Medicinal Chemistry, Modification of the hydroxy lactone ring of camptothecin*, vol. 32, No. 3, pp. 715–720 (1989).

J.R. Eckardt et al., "Topoisomerase I Inhibitors: Promising Novel Compounds," *Contemporary Oncology*, 47–60, Jan. 1993.

M.C. Wani, A.W. Nicholas, M.E. Wall, "Plant Antitumor Agents. 28. Resolution of a Key Tricyclic Synthon,5'(RS)–1, 5–Dioxo–5'–ethyl–5'–hydroxy–2'H,5'H,6'H–6'–oxopyrano [3',4'–f]$\Delta^{6,8}$–tetrahydroindolizine: Total Synthesis and Antitumor Activity of 20(S)–and 20(R)–Camptothecin," *J. Med. Chem.*, 2317–2319, v. 30, N. 12 (1987).

W.D. Kingsbury, "The Chemical Rearrangement of Camptothecin to Mappicine Ketone," *Tetrahedron Letters*, 6847–6850, v. 29, N. 52 (1988).

A. Ejjima, H. Terasawa, M. Sugimori, H. Tagawa, "Asymmetric Synthesis of (S)–Camptothecin[1]", *Tetrahedron Letters*, 2639–2640, v. 30, N. 20 (1989).

E. J. Corey, D. Crouse, J. Anderson, "A Total Synthesis of Natural 20 (S–)–Camptothecin",*J. Org. Chem.*, 2140–2141, v. 40, N. 14 (1975).

D. P. Curran and H. Lui, "New 4+1 Radical Annulations. A Formal Total Syntehsis of (±)–Camptothecin",*J. Am. Chem. Soc.*, 5863–5864, 114 (1992).

J. Quick, "A New Route to Pyridones Via Imines of Pyruvic Esters", *Tetrahedron Letters*, 327–330, N. 4 (1977).

(List continued on next page.)

*Primary Examiner*—Bernard Dentz
*Attorney, Agent, or Firm*—Frank P. Grassler

[57] ABSTRACT

A process for removal of heavy metal contaminants from organic compounds, especially campthothecin analogs.

7 Claims, No Drawings

OTHER PUBLICATIONS

D.E. Berry et al., "Naturally Occurring Inhibitors of Topoisomerase I Mediated DNA Relazation", *J. Org. Chem.*, 420–422, 57 (1992).

T. Sugasawa, T. Toyoda, and K. Sasakura, "A Total Synthesis of dl–Camptothecin", *Tetrahedron Letters*, 5109–5112, N. 50 (1972).

A.I.Meyers et al., "A Total Synthesis of Camptothecin and Deethyldeoxycamptothecin", *J. Org. Chem*, 1974–1982, V. 38, N. 11 (1973).

R.A. Earl and K.P.C. Vollhardt, "The Preparation of 2(1H)–Pyridinones and 2,3–Dihydro–5(1H)–indolizinones via Transition Metal Mediated Cocylization of Alkynes and Isocyanates. A Novel Construction of the Antitumor Agent Camptothecin"<*J. Org. Chem.*, 4786–4800, v. 49, N. 25 (1984).

T. Sugasawa, M. Adachi, K. Sasakura, and A. Kitagawa, "Aminohaloborane in Organic Synthesis.2. Simple Synthesis of Indoles and 1–Acyl–3–indolinones Using Specific Ortho α–Chloroacetylation of Anilines", *J. Org. Chem.*, 578–586, v. 44, N. 4 (1979).

M.C. Wani et al., "Plant Antitumor Agents. 18.[1] Synthesis and Biological Activity of Camptothecin Analogues", *J. Med. Chem.*, 554–560, v. 23, N.5 (1980).

M.C. Wani et al., "Plant Antitumor Agents.IX. The Total Synthesis of dl–Camptothecin", *J. Am. Chem. Soc.*, V. 94, N. 10 (1972).

M.C. Wani, A.W. Nicholas, and M.E. Wall, "Plant Antitumor Agents. 23.[1] Synthesis and Antileukemic Activity of Camptothecin Analogues," *J. Med. Chem.*, 2358–2363, V. 29, N. 11 (1986).

W.D. Kingsbury et al., "Synthesis of Water–Soluble (Aminoalkyl)camptothecin Analogues: Inhibition of Topoisomerase I and Antitumor Activity"<*J. Med. Chem.*, 98–107, V. 34, N. 1 (1991).

G.A. Crispino, et al., "Improved Enantioselectivity in Asymmetric Dihydroxylations of Terminal Olefins Using Pyrimidine Ligands", *J. Org. Chem.*, 3785–3786, V. 58, N. 15 (1993).

A.M. Klibanov, "Asymmetric Transformations Catalyzed by Enzymes in Organic Solvents", *Acc. Chem. Res.*, 114–120, V. 23, N. 4 (1990).

R.C. Larock, "Alkene and Alkyne Additions", *Comprehensive Organic Trnasformations: A Guide to Functional Group Preparations*, VCH Publications, New York (9189) Ch. 4.

R.F. Heck, "Double Bond Isomerization", *Palladium Reagents in Organic Syntheses*, Academic Press Inc., San Diego, CA (1987). Ch. 2.

P.A. Grieco, M. Nishizawa, N. Marinovic, W.J. Ehmann, "Remote Double Bond Migration via Rhodium Catalysis: A Novel Enone Transposition"<*J.Am. Chem. Soc.*, 7102–7104, V. 98, N. 22 (1976).

Comins, Daniel L., "The Synthesis of Analogs of Camptothecin"a thesis submitted to the University of New Hampshire (1977).

F. C. Fang et al., "Catalytic Enantioselective Synthesis of 20(S)–camptothecin: A Practical Application of the Sharpless Asymmetric Dihydroxylation Reactions", *Journal of Organic Chemistry*, V. 59, N. 21, (Oct. 21, 1994).

D.L. Comins et al., "Asymmetric Synthesis of Camptothecin Alkaloids: A Nine–step Synthesis of (S)–camptothecin", *Tetrahedron Letters*, V. 35, N. 30, (Jul. 1994).

Database WPI, Section CH, Week 8809, *Derwent Publications Ltd.*, London, GB; Class E11, AN88–059926, & JP 63 014 824 A (Tanaka Kikinzoku Kogyo), (Jan. 22, 1988).

METHOD OF REMOVING HEAVY METAL CONTAMINANTS FROM ORGANIC COMPOUNDS

This application is filed pursuant to 35 U.S.C. §371 as a United States National Phase Application of International Application No. PCT/US95/05425 filed 2 May 1995 which is a continuation of U.S. Ser. No. 08/237,081 filed 3 May 1994, now U.S. Pat. No. 5,491,237.

FIELD OF THE INVENTION

The present invention relates to novel chemical compounds that are useful as intermediates in the preparation of camptothecin and camptothecin-like compounds and to processes for their preparation.

BACKGROUND OF THE INVENTION

Useful camptothecin and camptothecin-like compounds that can be produced using intermediates and processes of the present Invention include compounds described in U.S. Pat. No. 4,894,456 to Wall et al. issued Jan. 16, 1990; U.S. Pat. No. 4,399,282 to Miyasaka, et al. issued Aug. 16, 1983; U.S. Pat. No. 4,399,276 to Miyasaka, et al. issued Aug. 16, 1983; U.S. Pat. No. 4,943,579 to Vishnuvajjala, et al. issued Jul. 24, 1990; European Patent Application 0 321 122 A2 filed by SmithKline Beckman Corporation, and published Jun. 21, 1989; U.S. Pat. No. 4,473,692 to Miyasaka, et al. issued Sep. 25, 1984; European Patent application No. 0 325 247 A2 filed by Kabushiki Kaisha Yakult Honsh, and published Jul. 26, 1989; European Patent application 0 556 585 A2 filed by Takeda Chemical Industries, and published Aug. 25, 1993; U.S. Pat. No. 4,981,968 to Wall, et al. issued Jan. 1, 1991; U.S. Pat. No. 5,049,668 to Wall, et al. issued Sep. 17, 1991; U.S. Pat. No. 5,180,722 to Wall, et al. issued Jan. 19, 1993 and European Patent application 0 540 099 A1, filed by Glaxo Inc., and published May 5, 1993.

Previous methods used in the preparation of camptothecin and camptothecin-like compounds employ resolutions or chiral auxiliaries to obtain enantiomerically enriched intermediates. A problem with these methods is that a resolution necessitates discarding half of the racemic material and a chiral auxiliary requires utilizing stoichiometric amounts of a chiral subunit to enantioselectively install the chiral center.

The present Invention describes a method for producing enantiomerically enriched intermediates useful for the preparation of camptothecin and camptothecin-like compounds using a process of catalytic asymmetric induction. In this process, a chiral catalyst used in sub-stoichiometric amounts influences the stereoselective formation of the chiral center. Additionally, the process continually regenerates the chiral catalyst preventing waste.

SUMMARY OF THE INVENTION

One aspect of the present invention is a process of providing novel compounds of Formula (I), which are useful as intermediates in the preparation of camptothecin and camptothecin-like compounds,

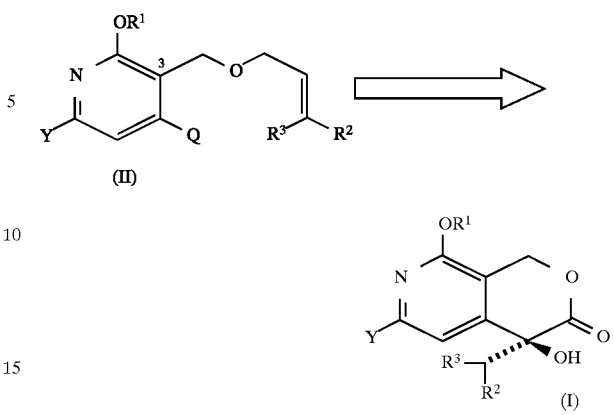

wherein:
R$^1$ represents alkyl, particularly methyl, R$^2$ represents H or alkyl, particularly methyl, R$^3$ represents H or alkyl, particularly H; Q represents triflate or halo particularly bromo and iodo more particularly iodo and Y represents chloro or OR$^4$, wherein R$^4$ represents alkyl or triflate, or particularly H.

In addition to a process for manufacturing the compounds of Formula (I), other aspects of the invention include the compounds of Formula (I) and various intermediates useful in producing the compounds of Formula (I). Other aspects and advantages of the present invention will become apparent from a review of the detailed description below.

DETAILED DESCRIPTION OF THE INVENTION

The term "alkyl" as used herein means, a linear or branched alkyl group with from 1 to about 8 carbon atoms, such as, but not limited to, methyl, ethyl, propyl, isopropyl, n-butyl, tert-butyl, hexyl and octyl. The terms "halo" and "halogen" as used herein refers to a substitutent which may be fluoro, chloro, bromo, or iodo. The term "triflate" as used herein refers to trifluoromethanesulphonate. The designation "C" as used herein means centigrade. The term "ambient temperature" as used herein means from about 20° C. to about 30° C.

Compounds of the present Invention have 1 or more asymmetric carbon atoms that form enantiomeric arrangements, i.e., "R" and "S" configurations. The present Invention includes all enantiomeric forms and any combinations of these forms. For simplicity, where no specific configuration is depicted in the structural formulas, it is to be understood that both enantiomeric forms and mixtures thereof are represented. Unless noted otherwise, the nomenclature convention, "(R)" and "(S)" denote essentially optically pure R and S enantiomers respectively. Also included in the present Invention are other forms of the compounds including: solvates, hydrates, various polymorphs and the like.

Acceptable salts include, but are not limited to salts with inorganic acids and bases such as hydrochloride, sulfate, phosphate, diphosphate, hydrobromide and nitrate or salts with organic acids such as acetate, malate, maleate, fumarate, tartrate, succinate, citrate, lactate, methanesulfonate, p-toluenesulfonate, palmoate, salicylate, oxalic and stearate. For further examples of acceptable salts see, "Pharmaceutical Salts," J. Pharm. Sci., 66(1), 1 (1977).

Thus, one aspect of the present Invention provides a process for preparing compounds of Formula (V);

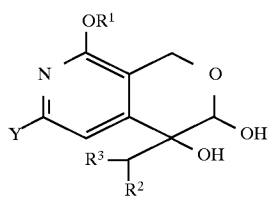

which comprises dihydroxlating a compound of Formula (III),

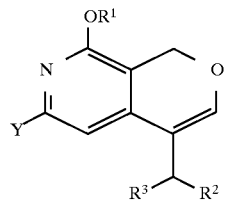

using a catalytic asymmetric dihydroxylation reaction. The reaction is carried out in the presence of an osmium catalyst (e.g., potassium osmate (VI) dihydrate, osmic chloride hydrate or osmium tetroxide), a chiral tertiary amine catalyst (e.g., derivatives of the cinchona alkaloids such as 2,5-diphenyl-4,6-bis(9-O-dihydroquinidyl)pyrimidine, a stoichiometric oxidizing reagent (e.g., potassium ferricyanide, hydrogen peroxide or N-methylmorpholine N-oxide), and a primary amide (e.g., methanesulfonamide) under basic conditions (e.g. potassium carbonate) in an aqueous mixture containing a polar protic solvent (e.g., t-butanol, i-propanol, n-propanol). The reaction should be carried out at a temperature of between about 0° C. to about 25° C. for about 24 to about 48 hours. Variations on these conditions will be apparent from the literature on the catalytic asymmetric dihydroxylation reaction. See, e.g., K. B. Sharpless et al., *J. Org. Chem.* 58, 3785–3786 (1993).

Alternatively the compound of Formula III is oxidized to a compound of Formula V in an achiral dihydroxylation reaction to yield a racemic cis-diol which is then resolved enzymatically to give the enantiomerically enriched compound of Formula V. See R. Larock, *Comprehensive Organic Transformations*, 493–496 (1989). The resolution reaction may be carried out in the presence of an acylating enzyme such as pancreatic lipases, *pseudomonas fluorenscens* lipases, *C. cylindracea* lipases, *Chromobacterium viscosum* lipases and *Aspergillus niger* lipases in the presence of an acylating agent such as vinyl acetate at a temperature of between about 0° C. to ambient temperature for about 2 to about 48 hours. Variations on these conditions will be apparent from A. Klibanov, *Asymmetric Transformations Catalyzed by Enzymes in Organic Solvents, Acc. Chem Res.* 1990, 23, 114–120.

Compounds of Formula (III) may be prepared by isomerizing a compound of Formula (IV).

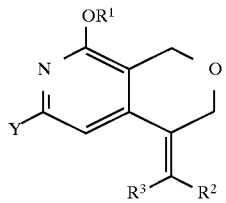

The isomerization is carried out under standard conditions used to isomerize double bonds, for example, in the presence of a metal catalyst (e.g. a rhodium catalyst such as tris(triphenylphosphine)rhodium(I) chloride under basic conditions in a polar aprotic solvent (e.g., acetonitrile or N,N-dimethylformamide) or a polar protic solvent (e.g., n-propanol, i-propanol, or t-butanol). The reaction should be carried out in an inert atmosphere, such as under nitrogen or argon gas in a suitable reaction vessel equipped with an overhead mechanical stirrer and water cooled condenser. The reaction mixture may be heated to a temperature between about 50° to about 110° C. for about 1 to about 24 hours. Variations on these conditions will be apparent from Grieco et. al, R. Heck, *Palladium Reagents in Organic Syntheses*, 19–22 (1990) and *Journal of the American Chemical Society*, 98:22, 7102–7104, 1976.

Compounds of Formula (IV) may be prepared by cyclizing a compound of Formula (II).

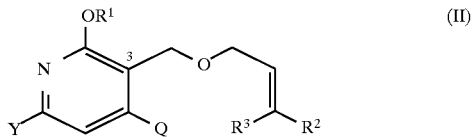

The compounds of Formula (II) may be cyclized by an intramolecular Heck reaction. The reaction may be carried out in the presence of a palladium catalyst (e.g., palladium (II) acetate) or a palladium catalyst and a rhodium catalyst (e.g. tris(triphenylphosphine) rhodium(I) chloride) under basic conditions in a polar aprotic solvent (e.g., acetonitrile or N,N-dimethylformamide) or a polar protic solvent (e.g., n-propanol, i-propanol, or t-butanol). A phase transfer catalyst such as a tetraalkylammonium halide salt (e.g., tetra-n-butyl ammonium chloride, tetra-n-butyl ammonium bromide, or tetra-n-butyl ammonium iodide) may be included especially when a polar aprotic solvent is used. A ligand for the palladium catalyst may also be included such as a triphenylphosphine, tri-o-tolyphosphine, tri-m-tolyphosphine or tri-p-tolyphosphine. The reaction should be carried out in an inert atmosphere, such as under nitrogen or argon gas in a suitable reaction vessel equipped with an overhead mechanical stirrer and water cooled condenser. The reaction mixture may be heated to a temperature between about 50° to about 110° C. for about 1 to about 24 hours. Variations on these conditions will be apparent from the literature on the Heck reaction. See, e.g., R. Grigg et al. *Tetrahedron* 46, 4003–4008 (1990).

The intermediates of Formula (V) may be oxidized to yield a compound of Formula (I).

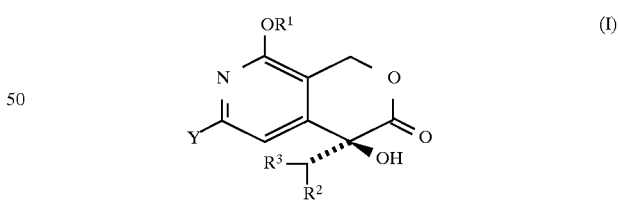

The reaction is carried out in the presence of an oxidizing reagent (e.g., bromine or iodine) in a polar protic medium (e.g., aqueous methanol, aqueous t-butanol or aqueous n-propanol) in the presence of a base (e.g., calcium carbonate) at a temperature of from about 0° C. to about 25° C.

The starting material, compounds of Formula II, may be produced by sequentially formylating and halogenating a halo-alkoxy-pyridine such as 2-methoxypyridine available from the Aldrich Chemical Company, Inc., 1001 West Saint Paul Avenue, Milwaukee, Wis. 53233, producing a halo-pyridinecarboxaldehyde. Formylation at the 3-position is disclosed in D. Comins and M. Killpack, *J. Org. Chem.* 55, 68–73 (1990). If an alkoxy-pyridine is being utilized the formylation may be carried out by deprotonation at the 3-position with a base such as t-butyllithium in tetrahydrofuran or dimethoxyethane at a temperature at least as low as about −60° C. The C-3-lithiated pyridine intermediate is then alkylated with a formamide such as N-formyl-N,N',N'-trimethylethylenediamine at a temperature of between about −60° C. and −20° C. The intermediate aminoalkoxy species is deprotonated at the C-4 position using a base such as n-butyllithium. The C-4-lithiated-pyridine intermediate can then be halogenated by mixing the intermediate with a solution of iodine or bromine in a polar or nonpolar organic solvent, preferably at a temperature of at least as low as about −60° C., to form an alkoxyaldehyde. The alkoxyaldehyde is then reduced in an alcoholic acidic media in the presence of a trialkylsilane to yield an alkoxymethylpyridine. The acid should be a strong non-oxidizing protic acid (e.g., sulfuric acid or trifluoroacetic acid) or a Lewis acid (e.g., boron trifluoride etherate) or an activated silylating reagent (e.g., trimethylsilyltrifluoromethanesulfonate). At least about 2 molar equivalents of an unsaturated alcohol (e.g., crotyl alcohol) should be included to convert the aldehyde to an ether of Formula (II). Conditions and variations on the silane reduction of aldehydes is described by M. Doyle et al., *J. Am. Chem. Soc.* 94:10, 3659–3661 (1972). The above reactions are further described in U.S. Pat. No. 5,254,690 to Comins et al. issued Oct. 19, 1993.

In a further particular aspect of the Invention, intermediates of Formula (III) are prepared by a single reaction comprising cyclizing and isomerizing a compound of Formula II by an intramolecular Heck reaction. The Heck reaction is carried out in the presence of a palladium catalyst (e.g., palladium acetate) or a palladium catalyst and a rhodium catalyst (e.g. tris(triphenylphosphine) rhodium(I) chloride) under basic conditions (e.g., potassium carbonate) in a polar aprotic solvent (e.g., acetonitrile or N,N-dimethylformamide) or in a polar-protic solvent (e.g., n-propanol, i-propanol, or t-butanol). A phase transfer catalyst such as a tetraalkylammonium halide salt (e.g. tetra-n-butyl ammonium chloride, tetra-n-butyl ammonium bromide, or tetra-n-butyl ammonium iodide) should be included when a polar-aprotic solvent is used. The reaction should be carried out in an inert atmosphere, such as under nitrogen or argon gas in a suitable reaction vessel equipped with an overhead mechanical stirrer and water cooled condenser. The reaction mixture may be heated to a temperature of between about 50° to about 110° C. for about 1 to about 24 hours. Variations on these conditions will be apparent from the literature on the Heck reaction. See, e.g., R. Grigg et al. *Tetrahedron* 46, 4003–4008 (1990).

In a still further particular aspect of the Invention, compounds of Formula (I) are prepared by a two-step one-pot sequence of reactions comprising: dihydroxylating and oxidizing the compounds of Formula (III). The dihydroxylation is a catalytic asymmetric dihydroxylation reaction carried out in the presence of an osmium catalyst (e.g., potassium osmate (VI) dihydrate, osmic chloride hydrate or osmium tetroxide), a chiral tertiary amine catalyst (e.g., derivatives of the cinchona alkaloids), a stoichiometric oxidizing reagent (e.g., potassium ferricyanide, hydrogen peroxide or N-methylmorpholine N-oxide), a primary amide (e.g., methanesulfonamide), under basic conditions (e.g., potassium carbonate) in an aqueous mixture containing a polar protic alcohol (e.g., t-butanol, i-propanol, n-propanol). The reaction is be carried out at a temperature between about 0° C. to about 25° C. for about 24 to about 48 hours. Variations on these conditions will be apparent from literature on the catalytic asymmetric dihydroxylation reaction. See, e.g., K. B. Sharpless et al., *J. Org. Chem.* 58, 3785–3786 (1993). The following step, an oxidation, is carried out on the above reaction mixture in the presence of an oxidizing reagent (e.g., bromine, iodine, chromium trioxide or pyridine sulfur trioxide) and a base (e.g., calcium carbonate or triethylamine) at a temperature between about 0° to about 25° C.

Thus, progressing compounds of Formula (II) to compounds of Formula (I) through the intermediate compounds of Formula (III) is schematically represented by the following reaction scheme:

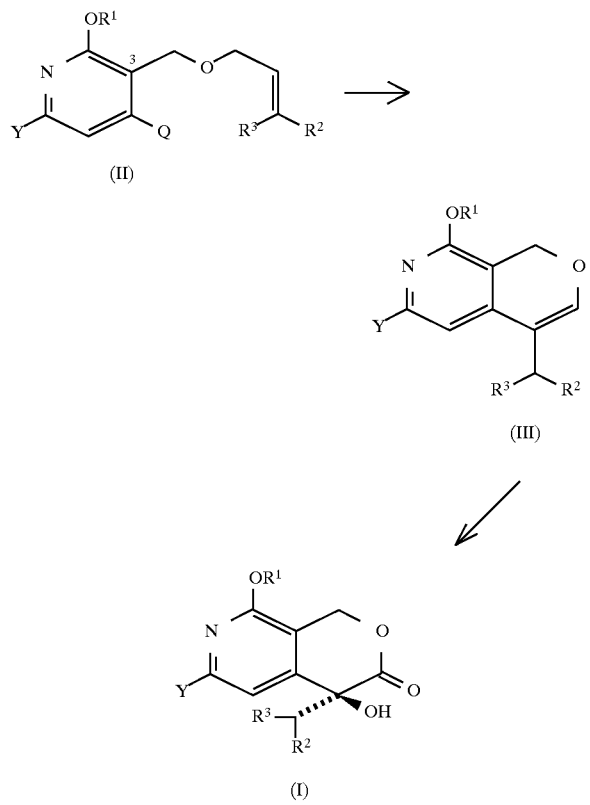

In a still further aspect of the Invention, the compounds of Formula (I) are prepared by a four-step one-pot sequence of reactions comprising i) cyclizing ii) isomerizing iii) dihydroxlating and iv) oxidizing a compound of Formula (II) as described herein.

A still further aspect of the present Invention is a method of removing heavy metal contamination from organic compounds produced by processes described herein. This heavy metal removal process is, moreover, applicable to other organic compounds. Heavy metals able to be removed employing this process include but are not limited to: palladium, osmium, iron, lead, cobalt, rhodium, chromium, manganese, mercury, copper, titanium, zinc, nickel and platinum. An example of the removal of the heavy metal catalyst palladium is exemplified herein.

The compounds of Formula (I), (II), (III), (IV) and (V) are novel and represent a still further aspect of the Invention.

The compounds of Formula (I) are useful as intermediates in the preparation of camptothecin and camptothecin-like derivatives such as those defined and described in European Patent application 0 540 099 A1, filed by Glaxo Inc., and published May 5, 1993. Thus, for example, a compound of Formula (I) may be demethylated under acidic or basic conditions to yield a compound of Formula (VI).

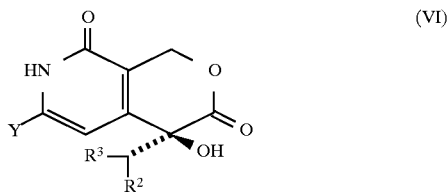

Racemic compounds of Formula (VI) are known and have been described in World Patent Application WO 92/11263, filed by North Carolina State University, and published Jul. 9, 1992, having utility as intermediates for the preparation of camptothecin derivatives.

A typical preparation and heavy metal contamination removal from a camptothecin derivative, utilizing an intermediate of Formula (I) is exemplified herein.

EXAMPLES

The following examples illustrate various aspects of the present Invention, but should not be construed as limitations. The symbols, conventions and nomenclature not specifically defined below are consistent with those used in the contemporary chemical literature, for example the journal of the *American Chemical Society*.

In the examples that follow: "mg" means milligram(s), "M" means molar, "mL" means milliliter(s), "mmol" means millimole(s), "L" means liter(s), "mol" means mole(s), "g" means gram(s), "TLC" means thin layer chromatography, "HPLC" means high pressure liquid chromotography, "mm" means millimole(s), "mp" means melting point, "MHz" means Megahertz, "$^1$H-NMR" means proton nuclear magnetic resonance, "Hz" means Hertz, "hr" or "h" means hour(s) and "N" means normal. Also included in the following examples is terminology commonplace with the use of a proton nuclear magnetic resonance spectrometer.

Unless otherwise noted all starting materials were obtained from commercial suppliers and used without further purification. All reactions involving oxygen or moisture-sensitive compounds were performed under a dry $N_2$ atmosphere. All reactions and chromatography fractions were analyzed by thin-layer chromatography on silica gel plates, visualized with UV light and $I_2$ stain.

$^1$H-NMR spectra were measured in $CDCl_3$ or DMSO-$d_6$ using either a Varian Gemini-200 MHz or a Bruker AMX-400 MHz instrument. J values are reported in Hertz. Chemical shifts are expressed in ppm in reference to an internal standard such as $CHCl_3$ or DMSO. Apparent multiplicities are designated as s, singlet; d, doublet; t, triplet; q, quartet; m, multiplet; b, broad. All mass spectra were taken in the positive ion mode under chemical ionization (CI), electron impact (EI), or by fast-atom bombardment (FAB). Melting points were determined on a Digital melting point apparatus, electrothermal series 1A9000, model 9200 and are uncorrected. Elemental analyses were performed by Atlantic Microlab, Norcross, Ga.

Example 1

4-iodo-2-methoxy-pyridine-3-carbaldehyde

A 5 liter 3-necked round bottom flask is equipped with an overhead mechanical stirrer under nitrogen, the flask is charged with tetrahydrofuran (1 L) and cooled to −78° C. To this stirred solution is added tert-butyllithium (1.7M in pentane, 800 mL, 1.36 mol) via canula followed by 2-methoxypyridine (132.2 g, 1.21 mol) at −78° C. The mixture is allowed to stir for one hr at −78° C. To the mixture is added N-formyl-N,N',N'-trimethylethylenediamine (176 mL, 1.37 mol) dropwise at −78° C. described as in Comins, D. L.; Baevsky, M. F.; Hong, H. *J. Am. Chem. Soc.* 1992, 114, 10972. The reaction mixture is stirred for about 30 min at −78° C. before warming to −23° C. over about 30 min. To the mixture at −23° C. is added ethylene glycol dimethyl ether (1 L) followed by n-butyllithium (2.5M in hexanes, 800 mL, 2.0 mol). The resultant mixture is stirred for about 2 h during which time the reaction mixture turns deep green. A 12 liter 4-neck round bottom flask is equipped with an overhead mechanical stirrer under nitrogen, the 12 liter flask is charged with iodine (571 g, 2.25 mol) and ethylene glycol dimethyl ether (2 L) and the resultant solution is cooled to −78° C. The contents of the 5 liter flask are transferred via canula to the mixture of iodine and ethylene glycol dimethyl ether in the 12 liter flask at −78° C. After the addition is complete, the reaction mixture is stirred for an additional 1 hr at −78° C. The cooling bath is removed and the mixture is allowed to warm to about 0° C. then treated with 2 L of water and 2 L of 1N hydrochloric acid. Methyl t-butyl ether (2 L) is added and the layers are separated. The aqueous layer is extracted with 2×1 L of methyl t-butyl ether. The combined organic extracts are washed with 1.2 L of saturated sodium thiosulfate solution followed by 1.2 L of saturated sodium chloride solution. The organic extracts are dried over sodium sulfate, filtered, and concentrated in vacuo to give a thick slurry. To the slurry is added 1 L of hexane resulting in the generation of additional precipitate. The mixture is cooled in an ice/water bath for about 30 min then filtered yielding 4-iodo-2-methoxy-pyridine-3-carbaldehyde. The filtrate is reconcentrated to a slurry and treated with hexane to generate additional precipitate again yielding 4-iodo-2-methoxy-pyridine-3-carbaldehyde. Chromatography (silica gel, 10% ethyl acetate/hexane) yields an analytical sample as a bright yellow solid: mp 98°–99° C. 1H-NMR (400 MHz, $CDCl_3$) 10.21 (s, 1H), 7.86 (d, J=5 Hz, 1H), 7.54 (d, J=5 Hz, 1H), 4.06 (s, 3H); IR ($CHCl_3$) 1710, 1560, 1470 1380, 1305, 1260, 1025 $cm^{-1}$; Elemental analysis: calculated for $C_7H_6NO_2I$: C 31.97%, H 2.30, N 5.32, I 48.25; Found: C 32.06, H 2.35; N 5.25, I 48.35.

Example 2

3-(but-2-enyloxymethyl)-4-iodo-2-methoxy-pyridine

A 500 mL 3-necked round-bottom flask is equipped with an overhead mechanical stirrer under nitrogen, the flask is charged with 4-iodo-2-methoxy-pyridine-3-carbaldehyde (75.0 g, 0.29 mol) prepared as in example 1, crotyl alcohol (75 mL, 0.88 mol), and triethylsilane (70 mL, 0.44 mol). To the stirred suspension at 0° C. is added trifluoroacetic acid (175 mL, 2.27 mol) dropwise via an addition funnel. The resulting solution is stirred at about 22° C. for approximately 12 hr. The reaction mixture is slowly poured into a rapidly stirring saturated sodium bicarbonate solution (2 L). The mixture is extracted with 3×500 mL of hexane. The combined organic layers are dried over sodium sulfate, filtered, and concentrated in vacuo to give an oil. Purification of this oil by vacuum distillation (about 0.4 mm Hg, about 120°–130° C.) yields 3-(but-2-enyloxymethyl)-4-iodo-2-methoxy-pyridine as a pale yellow oil: $^1$H-NMR (400 MHz, $CDCl_3$) δ7.69 (d, J=5 Hz, 1H), 7.34 (d, J=5 Hz, 1H), 5.71 (m, 2H), 4.58 (s, 2H), 4.02 (d, J=1 Hz, 2H), 3.94 (s, 3H), 1.72 (d, J=6 Hz, 3H); IR (neat) 2948, 2859, 1561, 1459, 1381, 1361, 1301, 1233, 1169, 1094, 1052 $cm^{-1}$; Elemental analysis: calculated for $C_{11}H_{14}NO_2I$: C 41.40, H 4.42, N 4.39, I 39.76; Found: C 41.31, H 4.45, N 4.37, I39.71.

Example 3

4-ethylidene-8-methoxy-3,4-dihydro-1H-pyrano[3,4-c]pyridine; 4-ethyl-8-methoxy-1H-pyrano[3,4-c]pyridine; 3(R)-4(S)-4-ethyl-8-methoxy-3,4-dihydro-1H-pyrano[3,4-c]pyridine-3,4-diol; 4(S)-4-ethyl-4-hydroxy-8-methoxy-1,4-dihydro-pyrano[3,4-c]pyridin-3-one A 5 liter 3-necked round bottom flask is equipped with an overhead mechanical stirrer under nitrogen, the flask is charged with 1-propanol (1.0 L), potassium carbonate (45.0 g, 0.33 mol), 3-(but-2-enyloxymethyl)-4-iodo-2-methoxy-pyridine (49.41 g, 0.16 mol) prepared as in example 2, and palladium(II) acetate (1.42 g, 6.33 mmol). The resulting slurry is heated at reflux for approximately 2 hr. During this time the color of the reaction mixture turns dark brown then light gray. A 150 mL aliquot of the reaction mixture is removed to identify 4-ethylidene- 8-methoxy-3,4-dihydro-1H-pyrano[3,4-c]pyridine and 4-ethyl-8-methoxy-1H-pyrano[3,4-c]pyridine.

This aliquot is diluted with 200 mL of tert-butyl methyl ether, filtered, and concentrated in vacuo affording a colorless oil. Chromatography on silica gel (5% ethyl acetate: hexanes) yields 4-ethyl-8-methoxy-1H-pyrano[3,4-c]pyridine. $^1$H-NMR (400 MHz, CDCl$_3$) δ8.04 (d, J=5.4 Hz, 1H), 6.65 (d, J=5.4 Hz, 1H), 6.54 (s, 1H), 5.04 (s, 2H), 3.94 (s, 3H), 2.32 (m, 2H), 0.97 (t, J=7.2 Hz, 3H), HRMS (EI$^+$): calc for C$_{11}$H$_{13}$NO$_2$: 191.0946, Found: 191.0952. IR(neat) 3450, 2962, 1731, 1602, 1581, 1454, 1390, 1362, 1313, 1267 cm$^{-1}$. Further elution gives 4-ethylidene-8-methoxy-3,4-dihydro-1H-pyrano[3,4-c]pyridine: $^1$H-NMR (400 MHz, CDCl$_3$) δ7.97 (d, J=6 Hz, 1H), 7.04 (d, J=6 Hz, 1H), 6.33 (q, J=7 Hz, 1H), 4.68 (s, 2H), 4.48 (s, 2H), 3.94 (s, 3H), 1.82 (d, J=2 Hz, 3H); MS (EI) 191 (M$^+$).

The reaction mixture is further treated with potassium ferricyanide (130 g, 0.40 mol), potassium carbonate (55.4 g, 0.40 mol), 2,5-diphenyl-4,6-bis(9-O-dihydroquinidyl) pyrimidine (1.16 g, 1.32 mmol) available from the Aldrich Chemical Company, Inc., 1001 West Saint Paul Avenue, Milwaukee, Wis. 53233, water (0.85 L) and methane sulfonamide (12.5 g, 0.13 mol). After cooling the mixture to 0° C., potassium (VI) osmate dihydrate (97 mg, 0.26 mmol) is added and the mixture is stirred for 2 days at 0° C.

A 300 ml aliquot of the reaction mixture is removed for identification of 3(R)-4(S)-4-ethyl-8-methoxy-3,4-dihydro-1H-pyrano[3,4-c]pyridine-3,4-diol. The aliquot is diluted with 150 mL of water and extracted with 3×50 mL of methylene chloride. The combined organic layers are washed with 2N potassium hydroxide. The aqueous layer is extracted with 100 mL of methylene chloride. The combined organic extracts are dried over sodium sulfate, filtered, and concentrated in vacuo giving a crude product. Chromatography of this material on silica gel using 5% methanol:methylene chloride provides an analytical sample of 3(R)-4(S)-4-ethyl-8-methoxy-3,4-dihydro-1H-pyrano[3,4-c]pyridine-3,4-diol: mp. 106°–107° C. (dec); $^1$H-NMR (400 MHz, CDCl$_3$) δ8.11 (d, J=5 Hz, 1H), 7.14 (d, J=5 Hz, 1H), 5.21 (d, J=5 Hz, 1H), 4.84 (d, J=16 Hz, 1H), 4.66 (d, J=16 Hz, 1H), 3.98 (s, 3H), 3.67 (d, J=5 Hz, 1H), 2.60 (s, 1H), 1.87 (q, J=8 Hz, 2H), 0.93 (t, J=8 Hz, 3H); IR 3450, 2948, 2375, 2360, 1604, 1580, 1459, 1403, 1368, 1267 cm$^{-1}$; Calculated for C$_{11}$H$_{14}$NO$_4$: 58.66% C, 6.71% H, 6.22% N; Found 58.75% C, 6.75% H, 6.26% N; [α]$_D^{22}$=−59.2 [c. 0.62, CHCl$_3$].

The reaction mixture is further treated with iodine (280 g, 1.10 mol) and calcium carbonate (54 g, 0.54 mol ) and allowed to stir 2 days at about 22° C. The reaction mixture is cooled to 0° C. and sodium sulfite (150 g, 1.19 mol) is added. After filtering the slurry through Celite 545® the filtrate is extracted with methylene chloride (3×200 mL) and the combined extracts are washed with brine. The organic phase is dried with sodium sulfate and then concentrated to an oil. The crude material is chromatographed (silica gel, 3% methanol/methylene chloride) to yield 4(S)-4-ethyl-4-hydroxy-8-methoxy-1,4-dihydro-pyrano[3,4-c]pyridin-3-one as amber colored oil: $^1$H-NMR (400 MHz, CDCl$_3$) δ8.21 (d, J=5 Hz, 1H), 7.16 (d, J=5 Hz, 1H), 5.58 (d, J=16 Hz, 1H), 5.27 (d, J=16 Hz, 1H), 3.99 (s, 3H), 3.62 (s, 1H), 1.80 (m, 2H), 0.96 (t, J=7 Hz, 3H); Calculated for C$_{11}$H$_{13}$NO$_4$: C 59.19, H 5.87, N 6.27; Found: C 59.11, H 5.91, N 6.16; IR (neat) 3480, 2977, 2952, 2360, 1744, 1603, 1592, 1457, 1378, 1379 cm$^{-1}$; [α]$_D^{22}$ +85.97°[c 0.677, CHCl$_3$]. Optical purity i determined to be a S/R ratio of 10:1 by chiral HPLC: 3% ethanol/hexane, 26° C., 1 mL/min., λ=300 nm, Chiralcel-OD column 250×4.6 mm. i.d.

Example 3a 4-ethyl-8-methoxy-1H-pyrano[3,4-c]pyridine

A mixture of 3-(but-2-enyloxymethyl)-4-iodo-2-methoxy-pyridine (228 g, 0.714 mol), potassium carbonate (200 g, 1.45 mol) and tetrabutylammonium chloride (100 g, 0.36 mol) in N,N-dimethylformamide (3.5 L) is purged with nitrogen for 20 min prior to the addition of palladium(II) acetate (3.75 g, 0.0167 mol) and tris(triphenylphosphine) rhodium(I) chloride (5.31 g, 0.00574 mol). The mixture is heated at 90° C. for about 4 h, cooled to below 50° C. and filtered through a pad of Celite®. The pad is washed with tert-butyl methyl ether (200 ml). The filtrate is washed with water (4×3 L), dried over sodium sulfate (260 g) and concentrated to a dark oil that is vacuum distilled (about 85°–98° C., about 6 mm Hg) to provide 4-ethyl-8-methoxy-1H-pyrano[3,4-c]pyridine as a yellow-orange oil which contains a 14.3:1 ratio of 4-ethyl-8-methoxy-1H-pyrano[3,4-c] pyridine to the corresponding double bond isomer, 4-ethylidene-8-methoxy-3,4-dihydro-1H-pyrano[3,4-c] pyridine.

Example 4

6-chloro-4-iodo-2-methoxy-3-(2-butenyloxymethyl) pyridine

A three-necked 500-mL round-bottom flask is equipped with a mechanical stirrer. Under nitrogen, the flask is charged with 6-chloro-4-iodo-2-methoxypyridine-3-carbaldehyde (53.0 g, 178 mmol) obtained as prepared in U.S. Pat. No. 5,254,690 to Comins et al. issued Oct. 19, 1993, triethylsilane (42.7 mL, 267 mmol) and crotyl alcohol (60.8 mL, 713 mmol). The slurry is cooled to 0° C. and trifluoroacetic acid (90.0 mL, 1.17 mmol) is added over 1 h. The reaction is allowed to warm to ambient temperature and stirred for 16 h. The reaction mixture is slowly poured into a rapidly stirred solution of saturated sodium bicarbonate in water (1.5 L). The mixture is extracted with methyl t-butyl ether (4×300 mL). The combined organic layers are washed with brine (700 mL) and dried over anhydrous sodium sulfate (150 g). The drying agent is removed by filtration and the solvents are removed in vacuo to afford 6-chloro-4-iodo-2-methoxy-3-(2-butenyloxymethyl)pyridine as crude product. The product can be purified by vacuum distillation to provide 6-chloro-4-iodo-2-methoxy-3-(2-butenyloxymethyl)pyridine as a light yellow oil. $^1$H NMR (200 MHz, CDCL3) δ1.75 (d, J=6.1 Hz, 3H), 3.92 (s, 3H), 4.00 (m, 2H), 4.59 (s, 2H), 5.74 (m, 1H) 5.75 (m, 1H), 7.39 (s, 1H).

Example 5

4-ethylidene-6-chloro-8-methoxy-3,4-dihydro-1H-pyrano[3,4-c]pyridine, 4-ethyl-6chloro-8-methoxy-1H-pyrano[3,4-c]pyridine; 3(R)-4(S)-4-ethyl-6-chloro-8-methoxy-3,4-dihydro-1H-pyrano[3,4-c]pyridine-3,4-diol; 4(S)-4-ethyl-4-hydroxy-6-chloro-8-methoxy-1,4-dihydro-pyrano[3,4-c]pyridin-3-one A 2-liter 3-necked round-bottom flask is equipped with an overhead stirrer under nitrogen, the flask is charged with 6-chloro-4-iodo-2-methoxy-3-(2-butenyloxymethyl)pyridine (26.8 g, 75.6 mmol), prepared as in example 4, anhydrous potassium carbonate (22.0 g, 159 mmol), palladium acetate (697 mg, 2.98 mmol), and 500 mL of 1-propanol. The mixture is brought to reflux for 1.5 hr. The reaction turned from an initial brown color to gray at approximately 1 hr. The reaction is allowed to cool to approximately 20° C. and a 166 mL aliquot of the reaction mixture is removed for purification and characterization of the initial products.

The aliquot (166 mL) taken above is diluted with 250 mL of tert-butyl methyl ether and stirred at ambient temperature for 20 min. The precipitates are removed by suction filtration and the filtrate is concentrated to give a yellow liquid. $^1$H NMR (400 MHz, CDCl$_3$) indicates 4-ethyl-6-chloro-8-methoxy-1H-pyrano[3,4-c]pyridine and 4-ethylidene-6-chloro-8-methoxy-3,4-dihydro-1H-pyrano[3,4-c]pyridine and chromatography on silica gel eluting with 3–5% EtOAc in hexane affords 4-ethylidene-6-chloro-8-methoxy-3,4-dihydro-1H-pyrano[3,4-c]pyridine as a white solid: $^1$H NMR (400 MHz, CDCl$_3$) δ1.85 (d, J=7.2 Hz, 3H), 3.97 (s, 3H), 4.48 (s, 2H), 4.66 (s, 2H), 6.35 (q, J=7.2 Hz, 1H), 7.10 (s, 1H). In addition crude 4-ethyl-6-chloro- 8-methoxy-1H-pyrano[3,4-c]pyridine is obtained and can be further purified by chromatography on silica gel. Elution with 2% EtOAc in hexane affords an analytical sample of 4-ethyl-6-chloro-8-methoxy-1H-pyrano[3,4-c]pyridine as a yellow liquid: $^1$H NMR (400 MHz, CDCl$_3$) δ1.13 (t, J=7.2 Hz, 3H), 2.26 (q, J=7.2 Hz, 3H), 3.97 (s, 3H), 5.03 (s, 2H), 6.56 (s, 1H), 6.66 (s, 1H). Elemental analysis: Calculated for C$_{11}$H$_{12}$ClNO$_2$: C 58.55, H 5.36, N 6.21, Cl 15.71. Found: C 58.65, H 5.39, N 6.22, Cl 15.63.

The rest of the reaction mixture is cooled to 0° C., followed by successive addition of potassium ferricyanide (49.8 g, 151 mmol), anhydrous potassium carbonate (21.1 g, 153 mmol), 2,5-diphenyl-4,6-bis(9-O-dihydroquinidyl)pyrimidine (448 mg, 0.502 mmol) available from the Aldrich Chemical Company, Inc., 1001 West Saint Paul Avenue, Milwaukee, Wis. 53233, methanesulfonamide (4.77 g, 50.4 mmol) and potassium osmate (VI) dihydrate (37.1 mg, 0.10 mmol). The brown slurry is stirred vigorously at 0° C. for about 58 hr. At this stage, a about 150 mL aliquot of the reaction mixture is taken for purification and characterization of the intermediate product. The aliquot (150 mL) taken from the reaction is treated with 25 g of sodium bisulfite and stirred for 20 min. The green mixture is diluted with water (200 mL) and extracted with CH$_2$Cl$_2$ (4×150 mL). The combined extracts are successively washed with 2N aq KOH (150 mL) and brine (300 mL), dried over anhydrous sodium sulfate, filtered, and concentrated in vacuo to give a residue. Chromatography on silica gel eluting with 5% MeOH in CH$_2$Cl$_2$ yields 3(R)-4(S)-4-ethyl-6-chloro-8-methoxy-3,4-dihydro-1H-pyrano[3,4-c]pyridine-3,4-diol as a white solid. mp 164°–166° C. [α]$_D$ −63.1° (c 1.30, MeOH).$^1$H NMR (400 MHz, CDCl$_3$) δ0.84 (t, J=7.5 Hz, 3H), 1.71 (q, J=7.5 Hz, 3H), 2.72 (s, 1H), 3.60 (d, J=4.7 Hz, 1H), 3.88 (s, 3H), 4.59 (ABq, J$_{AB}$=16.3 Hz, Δν=57.1 Hz, 2H), 5.10 (d, J=4.7 Hz, 1H), 7.08 (s, 1H), Elemental analysis: Calculated for C$_{11}$H$_{14}$ClNO$_4$: C 50.88, H 5.43, N 5.39, Cl 13.65. Found: C 50.98, H 5.41, N 5.34, Cl 13.70.

The rest of the reaction mixture is treated with iodine (95.9 g, 378 mmol) and calcium carbonate (18.9 g, 189 mmol). The mixture is warmed to ambient temperature and stirred for 48 hr. After being treated with 45 g of sodium sulfite (added in 4 portions over 40 min), the brown mixture is stirred for 1 hr. and turns green. Filtration of the reaction mixture by suction through a short pad of Celite 545® and washing with CH$_2$Cl$_2$ (5×300 mL) gives a two-phase mixture. The mixture is extracted with CH$_2$Cl$_2$ (3×500 mL). The combined organic phases are washed with brine (1 L), dried over anhydrous sodium sulfate and concentrated in vacuo to give a yellow oil which partially solidifies upon standing. The oil is chromatographed on silica gel. Elution with 2% MeOH in CH$_2$Cl$_2$ affords 4(S)-4-ethyl- 4-hydroxy-6-chloro-8-methoxy-1,4-dihydro-pyrano[3,4-c]pyridin-3-one which is a semi-solid at approximately 25° C. $^1$H NMR shift study with Eu(hfc)$_3$ indicates an 8.5:1 ratio of the S:R enantiomers. The absolute stereochemistry is determined by transformation to a known compound (vide infra). [α]$_D$ +62.4° (c 1.60, CHCl$_3$). $^1$H NMR (400 MHz, CDCl$_3$) δ0.99 (t, J=7.4 Hz, 3H), 1.82 (q, J=7.4 Hz, 2H), 3.68 (s, 1H), 4.03 (s, 3H), 5.40 (ABq, J$_{AB}$=15.6 Hz, Δν=120 Hz, 2H), 7.22 (s, 1H). Elemental analysis: Calculated for C$_{11}$H$_{12}$ClNO$_4$: C 51.28, H 4.69, N 5.44, Cl 13.76. Found: C 51.20, H 4.68, N 5.38, Cl 13.84.

Example 6

4-ethyl-8-methoxy-1H-pyrano[3,4-c]pyridine

A 3-liter 3-necked round bottom flask is equipped with a heating mantle monitored by a J-KEM thermocouple and an overhead stirrer; under nitrogen, the flask is charged with 3-(but-2-enyloxymethyl)-4-iodo-2-methoxy-pyridine (30.0 g, 93.9 mmol), prepared as in example 2, and 939 mL (0.1M) of N,N-dimethylformamide, followed by successive addition of anhydrous potassium carbonate (26.0 g, 188 mmol), palladium acetate (422 mg, 1.88 mmol) and tetra-n-butylammonium chloride (13.1 g, 47.0 mmol). The light brown mixture is brought to 90° C. and stirred for 30 min. The now dark brown mixture is allowed to cool to 85° C. and stirring is continued for 20 h when TLC (10% EtOAc/hexane) indicates complete reaction. After being cooled to ambient temperature, the mixture is filtered through Celite 545® (80 g), washed with MTBE (0.5 L) and the filtrate is poured into 800 mL of ice water and extracted with MTBE (3×600 mL). The combined extracts are successively washed with water (700 mL) and brine (700 mL), dried over anhydrous Na$_2$SO$_4$ (150 g). Evaporation in vacuo yields crude 4-ethyl-8-methoxy-1H-pyrano[3,4-c]pyridine $^1$H NMR (400 MHz) indicates an endo/exo ratio of 8:1. Vacuum distillation at about 112°–120° C. yields 4-ethyl-8-methoxy-1H-pyrano[3,4-c]pyridine as an 11:1 endo/exo mixture. $^1$H-NMR (400 MHz, CDCl$_3$) δ8.04 (d, J=5.4 Hz, 1H), 6.65 (d, J=5.4 Hz, 1H), 6.54 (s, 1H), 5.04 (s, 2H), 3.94 (s, 3H), 2.32 (m, 2H), 0.97 (t, J=7.2 Hz, 3H), HRMS (EI$^+$): calc for C$_{11}$H$_{13}$NO$_2$: 191.0946, Found: 191.0952. IR 3450, 2962, 1731, 1602, 1581, 1454, 1390, 1362, 1313, 1267 cm$^{-1}$

Example 7

4(S)-4-ethyl-4-hydroxy-8-methoxy-1,4-dihydro-pyrano[3,4-c]pyridin-3-one

A 2-liter 3-necked round bottom flask is equipped with an overhead stirrer and a cryocool monitored by a J-KEM thermocouple. The flask is successively charged with 200 mL of t-butyl alcohol, 261 mL water, potassium ferricyanide (51.7 g, 157 mmol), anhydrous potassium carbonate powder (21.7 g, 157 mmol), potassium osmate (VI) dihydrate (38.5 mg, 0.105 mmol), 2,5-diphenyl-4,6-bis(9-O-dihydroquinidyl)pyrimidine (461 mg, 0.523 mmol) Aldrich Chemical Company, Inc., 1001 West Saint Paul Avenue, Milwaukee, Wis. 53233, and methanesulfonamide (4.97 g, 52.3 mmol). After being stirred for 3 min. at ambient temperature, the slurry was cooled to 0° C., followed by addition of 4-ethyl-8-methoxy-1H-pyrano[3,4-c]pyridine (10.0 g, 52.3 mmol), prepared as in example 6, in 61 mL of t-butyl alcohol. The thick slurry is vigorously stirred for 48 h at which time TLC (10% EtOAc/hexane for enol ether, and 30% EtOAc/hexane or 10% MeOH/CHCl$_3$ for the diol product) and $^1$H NMR (400 MHz) on an aliquot indicate complete reaction. It is noted that the exo enol ether (4-ethylidene-8-methoxy-3,4-dihydro-1H-pyrano[3,4-c]pyridine) does not react to a significant extent.

The mixture is treated with iodine (133 g, 523 mmol) and calcium carbonate (26.2 g, 261 mmol). After being warmed to ambient temperature the thick slurry is stirred for 48 h. The mixture is cooled to 12° C. and sodium sulfite (70 g) is added in four portions over 20 min with ice cooling. The brown mixture is stirred for 15 min and turns green. Filtration by suction through a pad of Celite 545® (70 g) and extensive washing with CH$_2$Cl$_2$ (1.0 L) gives a two phase mixture. The water phase is extracted with CH$_2$Cl$_2$ (3×800 mL). The combined organic phases are washed with brine (1.2 L), dried over anhydrous Na$_2$SO$_4$ (180 g) and concentrated in vacuo to give 12.0 g of crude product as a yellow oil which does not solidify upon standing at ambient temperature. The oil is chromatographed on 150 g of silica gel. Elution with less than one liter of 2% MeOH in CH$_2$Cl$_2$ yields 4(S)-4-ethyl-4-hydroxy-4,7-dihydro-4,7-dihydro-1H-pyrano[3,4-c]pyridin-3,8-dione as a yellow oil. Chiral HPLC (Chiracel OD, EtOH/hexane 3:97, λ254 nm) shows a S/R ratio of 39:1. This ratio is confirmed by $^1$H NMR (400 MHz) shift study with Eu(hfc)$_3$, in which a S/R ratio of 37:1 is demonstrated. In addition, 1.95 g of product is collected as a mixture of the desired lactone product and faster moving impurities.

Example 8

4-ethyl-8-methoxy-1H-pyrano[3,4-c]pyridine

A warmed solution of 4-ethylidene-8-methoxy-3,4-dihydro-1H-pyrano[3,4-c]pyridine, prepared as in example 3 (0.35 g, 1.83 mmol) in 30 mL of n-propanol is purged with a stream of nitrogen for 20 minutes prior to the addition of tris(triphenylphosphine)rhodium(I) chloride (0.025 g, 0.027 mmol). The reaction mixture is stirred at reflux for 15 hours under nitrogen and again treated with tris(triphenylphosphine)rhodium(I) chloride (0.025 g). After 2 hr, the flask is charged with potassium carbonate (0.50 g, 3.60 mmol), and heated for 2 hr. The mixture is then treated with tris(triphenylphosphine)rhodium(I) chloride (0.025 g). The mixture is heated to reflux for an additional 2 hr, filtered through Celite 545® and the filtrate is concentrated in vacuo. $^1$H NMR analysis shows an 1:8.3 ratio of exo-(4-ethylidene-8-methoxy-3,4-dihydro-1H-pyrano[3,4-c]pyridine) to endocyclic (4-ethyl-8-methoxy-1H-pyrano[3,4-c]pyridine) product. The dark residue is chromatographed on silica gel using 5% EtOAc/hexanes to provide 4-ethyl-8-methoxy-1H-pyrano[3,4-c]pyridine, the endocyclic form, as a colorless oil. $^1$H-NMR (CDCl$_3$, 400 MHz): δ1.13 (t, J=7.4 Hz, 3H, —CH$_3$); 2.30 (q, J=7.4 Hz, 2H, —CH$_2$—); 3.95 (s, 3H, —OCH$_3$); 5.04 (s, 2H, —CH$_2$O); 6.55 (d, J=5.4 Hz, 1H, Aromatic); 8.04 (d, J=5.4 Hz, Aromatic). Anal. Calcd for C$_{11}$H$_{13}$NO$_2$.0.10CHCl$_3$.0.05C$_3$H$_8$O: C, 65.54; H, 6.60; N,6.79. Found: C, 65.48; H, 6.57; N, 6.89. Mass Spectrum (FAB+): m/e 192 (M+1,100%).

Example 9

4-ethyl-8-methoxy-3,4-dihydro-1H-pyrano[3,4-c]pyridine-cis-3,4-diol

A 25-mL round bottom flask, equipped with a magnetic stirring bar, is successively charged with N-methylmorpholine-N-oxide (826 mg, 7.05 mmol), acetone (1.3 mL), water (3.3 mL), t-butyl alcohol (0.6 mL) and 4% wt osmium tetroxide (water solution, 133 mg). The mixture is cooled to 0° C., followed by addition of 4-ethyl-8-methoxy-1H-pyrano[3,4-c]pyridine (1.50 g, 6.65 mmol), prepared as in example 8. The mixture is allowed to warm to ambient temperature and stirred for 20 h. A slurry of 100 mg of Na$_2$SO$_3$, 800 mg of talc and 4.6 mL of water is added. After being stirred for 10 min, the mixture is filtered through a short pad of Celite 545® and washed with 20 mL of 10% MeOH in CHCl$_3$. The filtrate is neutralized with 2N HCl to near pH 7 and diluted with about 20 mL of brine. The aqueous layer is extracted with 10% MeOH in CHCl$_3$ (2×15 mL) and the combined organic layers are dried over anhydrous Na$_2$SO$_4$ and concentrated in vacuo to afford crude product. Recrystallization from methanol-methyl t-butyl ether yields 4-ethyl-8-methoxy-3,4-dihydro-1H-pyrano[3,4-c]pyridine-cis-3,4-diol as a crystalline solid. $^1$H NMR (400 MHz, CDCl$_3$) δ0.93 (t, J=7.6 Hz, 3H), 1.87 (q, J=7.6 Hz, 2H), 2.63 (s, 1H), 3.45 (d, J=5.1 Hz, 1H), 3.98 (s, 3H), 4.75 (ABq, J$_{AB}$=16.4 Hz, Δv=68.0 Hz, 2H), 5.21 (d, J=5.1 Hz, 1H), 7.14 (d, J=5.2 Hz, 1H), 8.11 (d, J=5.2 Hz, 1H).

Example 10

3(R)-4(S)-4-ethyl-8-methoxy-3,4-dihydro-1H-pyrano[3,4-c]pyridine-3,4-diol; 3(R)-4(R)-4-ethyl-4-hydroxy-8-methoxy-3,4-dihydro-1H-pyrano[3,4-c]pyridine-3-yl ester A 10 mL round bottom flask is equipped with a magnetic stirring bar. The flask is charged with racemic 4-ethyl-8-methoxy-3,4-dihydro-1H-pyrano[3,4-c]pyridine-cis-3,4-diol (100 mg, 0.444 mmol), prepared as in example 9 and 100 mg of lipase from Candida cylindracea enzyme (Type VII, Sigma L-1754), followed by addition of 5 mL of vinyl acetate. The suspension is stirred at ambient temperature for 24 h. The mixture is filtered and the solids are washed with 20 mL of methylene chloride. The combined filtrates are concentrated in vacuo. The resultant residue is washed with 30% EtOAc in hexane. Filtration gives a white solid which is a mixture of 3(R)-4(S)-4-ethyl-8-methoxy-3,4-dihydro-1H-pyrano[3,4-c]pyridine-3,4-diol and acetic acid 3(R)-4(R)-4-ethyl-4-hydroxy-8-methoxy-3,4-dihydro-1H-pyrano[3,4-c]pyridine-3-yl ester as indicated by $^1$H NMR spectrum. Chromatography on silica gel yields (50%) of 3(R)-4(S)-4-ethyl-8-methoxy-3,4-dihydro-1H-pyrano[3,4-c]pyridine-3,4-diol and (42%) of 3(R)-4(R)-4-ethyl-4-hydroxy-8-methoxy-3,4-dihydro-1H-pyrano[3,4-c]pyridine-3-yl ester. The optical purity (80% ee) of 3(R)-4(S)-4-ethyl-8-methoxy-3,4-dihydro-1H-pyrano[3,4-c]pyridine-3,4-diol is determined by examination of the chiral HPLC and $^1$H NMR chiral shift study on 4(S)-4-ethyl-4-hydroxy-8-methoxy-1,4-dihydro-pyrano[3,4-c]pyridin-3-one derived from 3(R)-4(S)-4-ethyl-8-methoxy-3,4-dihydro-1H-pyrano[3,4-c]pyridine-3,4-diol. A shift study on acetic acid 3(R)-4(R)-4-ethyl-4-hydroxy-8-methoxy-3,4-dihydro-1H-pyrano[3,4-c]pyridine-3-yl ester with Eu(hfc)$_3$ indicates one enantiomer. 3(R)-4(S)-4-ethyl-8-methoxy-3,4-dihydro-1H-pyrano[3,4-c]pyridine-3,4-diol: mp 138° C. (dec.). $[\alpha]\Delta=-52.1°$ (MeOH, c 1.44). $^1$H NMR (CDCl$_3$, 400 MHz): δ0.93 (t, J=7.6 Hz, 3H), 1.87 (q, J=7.6 Hz, 2H), 2.63 (s, 1H), 3.45 (d, J=5.1 Hz, 1H), 3.98 (s, 3H), 4.75 (ABq, J$_{AB}$=16.4 Hz, Δν=68.0 Hz, 2H), 5.21 (d, J=5.1 Hz, 1H), 7.14 (d, J=5.2 Hz, 1H), 8.11 (d, J=5.2 Hz, 1H). Elemental analysis: Calculated for C$_{13}$H$_{17}$NO$_5$: C 58.66, H 6.71, N 6.22. Found: C 58.75, 6.74, N6.17. Acetic acid 3(R)-4(R)-4-ethyl-4-hydroxy- 8-methoxy-3,4-dihydro-1H-pyrano[3,4-c]pyridine-3-yl ester: mp 141°–143° C. $[\alpha]_A=+92.1°$ (MeOH, c 1.27).$^1$H NMR (CDCl$_3$, 400 MHz) δ0.89 (t, J=7.5 Hz, 3H), 1.76 (m, 2H), 2.01 (s, 3H), 2.07 (s, 1H), 3.89 (s, 3H), 4.61(ABq, J$_{AB}$=16.6 Hz, Δν=27.3 Hz, 2H), 6.09 (s, 1H), 7.04 (d, J=5.3 Hz, 1H), 8.03 (d, J=5.3 Hz, 1H). HRMS (EI+), Calculated for C$_{13}$H$_{17}$INO$_5$: 267.1104 Found: 267.1107.

Example 11

4(S)-4-ethyl-4-hydroxy-8-methoxy-1,4-dihydro-pyrano[3,4-c]pyridin-3-one

A 10-mL round bottom flask is equipped with a magnetic stirring bar. The flask is charged with a mixture of 3(R)-4(S)-4-ethyl-8-methoxy-3,4-dihydro-1H-pyrano[3,4-c]pyridine-3,4-diol (50 mg, 0.222 mmol), prepared as in example 10, calcium carbonate (386 mg, 3.86 mmol) and iodine (1.95 g,7.68 mmol) in 4 mL of MeOH—H$_2$O (10:1). The mixture is stirred at ambient temperature for 40 h, then poured into 10 mL of saturated sodium metabisulfate. The mixture is extracted with 10% MeOH/CH$_2$Cl$_2$ (3×10 mL). The combined extracts are washed with brine (10 mL), dried over anhydrous sodium sulfate and concentrated in vacuo yielding 4(S)-4-ethyl-4-hydroxy-8-methoxy-1,4-dihydro-pyrano[3,4-c]pyridin-3-one as a yellow oil. Chiral HPLC (Chiracel OD 250×16, 254 nm, 3% EtOH/hexane) and $^1$H NMR shift study with Eu(hfc)$_3$ both indicate a ratio of 9:1 (80% ee). $[\alpha]_D=+74.0°$ (CHCl$_3$, c 2.50). $^1$H NMR (CDCl$_3$, 400 MHz) δ0.89 (t, J=7.4 Hz, 3H), 1.72 (q, J=7.4 Hz, 2H), 3.55 (s, 1H), 3.93 (s, 3H), 5.36 (ABq, J$_{AB}$=15.5 Hz, Δν=125 Hz, 2H), 7.09 (d, J=5.3 Hz, 1H), 8.14 (d, J=5.3 Hz, 1H).

Example 12

4(S)-4-ethyl-4-hydroxy-6-chloro-4,7-dihydro-1H-pyrano[3,4-c]pyridin-3,8-dione

A 50-mL round bottom flask, equipped with a magnetic stirring bar, a water cooled condenser and an oil bath, is charged with 4(S)-4-ethyl-4-hydroxy-6-chloro-8-methoxy-1,4-dihydro-pyrano[3,4-c]pyridin-3-one (500 mg, 1.94 mmol), prepared as in example 5, and 20 mL of 6N aqueous HCl. The mixture is brought to reflux for 6 hr. Water is removed in vacuo at 45° C. The solid residue is dissolved in 15 mL of 10% MeOH in CHCl$_3$ and filtered through a short pad of silica gel eluting with 10% MeOH in CHCl$_3$ yielding 4(S)-4-ethyl-4-hydroxy-6-chloro-4,7-dihydro-1H-pyrano[3,4-c]pyridin-3,8-dione as a solid after concentration: mp 208°–209° C. $[\alpha]_D^{25}+58.1°$ (c 1.98, MeOH). (literature for optically pure 4(S)-4-ethyl-4-hydroxy-6-chloro-4,7-dihydro-1H-pyrano[3,4-c]pyridin-3,8-dione, $[\alpha]_D^{23}$ +58.5° (c 0.85, MeOH), $[\alpha]_D^{23}$ +71.9° (c 2.00, MeOH) see Comins, D. L.; Baevsky, M. F.; Hong, H. *J. Am. Chem. Soc.* 1992, 114, 10971). $^1$H NMR (400 MHz, DMSO-d6) δ0.80 (t, J=7.3 Hz, 3H), 1.78 (m, 2H), 5.37 (ABq, J$_{AB}$=5.6 Hz, Δν=42.6 Hz, 2H), 6.42 (s, 1H), 6.92 (s, 1H), 12.3 (br. s, 1H). c 0.67). $^1$H NMR (D$_2$O, 400 MHz) δ0.92(t, J=7.2 Hz, 3H), 1.89 (m, 2H), 2.55 (m, 2H), 2.81 (s, 3H), 2.96 (m, 2H), 3.11 (m, 2H), 3.41 (m, 3H), 3.71 (s, 2H), 5.32 (ABq, J$_{AB}$=16.1 Hz, Δν=54.2 Hz, 2H), 6.84 (s, 1H), 6.97 (s, 1H), 7.00 (s, 1H). Elemental analysis: Calculated for C$_{28}$H$_{30}$N$_4$O$_6$. 2HCl .H$_2$O: C 55.18, H 5.62, N 9.19, Cl 11.63. Found: C 55.41, H 5.70, N 9.24, Cl 11.52.

Example 13

7-(4-methylpiperazinomethylene)-10,11-ethylenedioxy-20(S)-camptothecin dihydrochloride Example 13a 1-(7-amino-2,3-dihydro-benzo[1,4]dioxin-6-yl)-2-chloro-ethanone A 4-necked 12-L round-bottom flask is equipped with a mechanical stirrer and water-cooled condenser. Under nitrogen, the flask is charged with 1M boron trichloride in methylene chloride (4 L, 4.00 mol). The solution is cooled to −20° C., then 1,4-benzodioxane-6-amine (500 g, 3.31 mol) available from the Aldrich Chemical Company, Inc., 1001 West Saint Paul Avenue, Milwaukee, Wis. 53233, is added as a solution in methylene chloride (250 mL) over 30 min. The temperature increases to 10° C. during the addition and is subsequently re-cooled back to −10° C. Chloroacetonitrile (250 mL, 3.95 mol) is added over 5 min, followed by addition of aluminum chloride (485 g, 3.64 mol). The resulting dark mixture is heated at reflux for 24 h. The reaction mixture is cooled to ambient temperature and transferred to two 20-L separatory funnels, each containing 10 L of water. After being stirred for 2.5 h, the organic layer is separated and the aqueous layer is extracted with methylene chloride (4×4 L). The combined organic layers are washed with brine (4 L), dried over anhydrous sodium sulfate and concentrated in vacuo. The resultant thick brown slurry is successively treated with 600 mL of methylene chloride and 2 L of hexane. The mixture is stirred at 0° C. for 30 min. The precipitate is collected by filtration on a Büchner funnel, washed with hexane (1 L) and dried in vacuo. at 30° C. yielding 1-(7-amino-2,3-dihydro-benzo[1,4]dioxin-6-yl)-2-chloro-ethanone as a yellow powder. Reverse HPLC (Spherisorb ODS-25 micron, 1:1 MeCN—H$_2$O) indicated a purity of 91%. Recrystallization from CH$_2$Cl$_2$ provides an analytical sample as a yellow crystalline solid: mp 130° C. (dec.). $^1$H NMR (CDCl$_3$, 200 MHz) δ4.24 (m, 2H), 4.32 (m, 2H), 4.59 (s, 2H), 6.21 (s, 1H), 6.23 (br. s, 2H), 7.29 (s, 1H). Elemental analysis: Calculated for C$_{10}$H$_{10}$ClNO$_3$: C 52.76, H 4.43, N 6.15. Found: C 52.62, H 4.42, N 6.12.

Example 13b 9-chloromethyl-7-oxo-2,3,6,7-tetrahydro[1,4]dioxino[2,3-g]quinoline-8-carboxylic acid methyl ester A 4-necked 12-L round-bottom flask is equipped with a mechanical stirrer and 500-mL addition funnel. Under nitrogen, the flask is charged with 1-(7-amino-2,3-dihydro-benzo[1,4]dioxin-6-yl)-2-chloro-ethanone (595 g, 2.61 mol), prepared as in example 13a, triethylamine (474 mL, 3.40 mol), and anhydrous acetonitrile (3.5 L). The solution is cooled to 0° C., then methyl malonyl chloride (364 mL, 3.40 mol) is added over 35 min. The cooling bath is removed and the mixture is stirred for 5 h. To the resultant slurry is added 25% sodium methoxide in methanol (596 mL, 2.61 mol) over 10 min. After being stirred at ambient temperature for 2 h, the now very thick yellow slurry is diluted with water (3 L). The precipitate is collected on a Büchner funnel and washed with water (3 L). The yellow solid is dried in vacuo. at 60° C. yielding 9-chloromethyl-7-oxo-2,3,6,7-tetrahydro[1,4]dioxino[2,3-g]quinoline-8-carboxylic acid methyl ester as a yellow solid. This crude product is used for the next step without further purification. Recrystallization from MeOH-DMSO (1:1) gave an analytical sample: mp>300° C. (dec.). $^1$H NMR (DMSO-d6, 400 MHz) δ3.85 (s, 3H), 4.32 (s, 2H), 4.36 (s, 2H), 4.83 (s, 2H), 6.83 (s, 1H), 7.40 (s, 2H), 12.0 (s, 1H). Elemental analysis: Calculated for $C_{10}H_{10}ClNO_3$: C 54.29, H 3.91, N 4.52. Found: C 53.68, H 3.84, N 4.48. HRMS (EI+): Calculated for $C_{10}H_{10}ClNO_3$: 309.0404. Found: 309.0405.

Example 13c 7-chloro-9-chloromethyl-2,3-dihydro[1,4]dioxino[2,3-g]quinoline-8-carboxylic acid methyl ester A 4-necked 5-L round-bottom flask is equipped with a mechanical stirrer and water-cooled condenser. Under nitrogen, the flask is charged with 9-chloromethyl-7-oxo-2,3,6,7-tetrahydro[1,4]dioxino[2,3-g]quinoline-8-carboxylic acid methyl ester (360 g, 1.16 mol), prepared as in example 13b, as a suspension in phosphorus oxychloride (1.8 kg). The mixture is heated to reflux generating a black solution. After being heated at reflux for 20 h, the reaction mixture is allowed to cool to ambient temperature and transferred to a 25-L separatory funnel containing 18 L of ice water. After being stirred vigorously for 1.5 h, the precipitate is collected on a Büchner funnel, washed with water (3 L) and dried in vacuo. at 50° C. yielding 7-chloro-9-chloromethyl-2,3-dihydro[1,4]dioxino[2,3-g]quinoline-8-carboxylic acid methyl ester as a dark crystalline solid: mp 130°–132° C. $^1$H NMR (CDCl$_3$, 200 MHz) δ4.05 (s, 3H), 4.42 (s, 4H), 4.81 (s, 2H), 7.50 (s, 2H). Elemental analysis: Calculated for $C_{14}H_{11}Cl_2NO_4$: C 51.24, H 3.38, N 4.27. Found: C 51.10, H 3.34, N 4.33.

Example 13d

[7-chloro-9-(4-methyl-piperazin-1-yl-methyl)-2,3-dihydro[1,4]dioxino[2,3-g]quinoline-8-carboxylic acid methyl ester A 4-necked 5-L round-bottom flask is equipped with a mechanical stirrer and 250-mL addition funnel. Under nitrogen, the flask is charged with 7-chloro-9-chloromethyl-2,3-dihydro[1,4]dioxino[2,3-g]quinoline-8-carboxylic acid methyl ester (340 g, 1.04 mol), prepared as in example 13c, and methylene chloride (2 L). To the stirred solution is added N-methylpiperazine (237 mL, 2.14 mol) over 10 min. After the addition is complete, the reaction mixture is stirred at ambient temperature for 15 h. The reaction mixture is poured into water (3 L) and the organic layer is separated. The aqueous layer is extracted with methylene chloride (3×2 L). The combined organic layers are washed with brine (2 L), dried over anhydrous sodium sulfate and concentrated in vacuo. The resultant thick brown slurry is successively treated with methylene chloride (300 mL) and hexane (1.5 L). The mixture is swirled at 0° C. for 30 min. The precipitate is collected on a Büchner funnel, washed with hexane (1 L) and dried in vacuo. at 30° C. yielding [7-chloro-9-(4-methyl-piperazin-1-yl-methyl)-2,3-dihydro [1,4]dioxino[2,3-g]quinoline-8-carboxylic acid methyl ester as a yellow powder: mp 143° C. $^1$H NMR (CDCl$_3$, 200 MHz) δ2.28 (s, 3H), 2.38–2.49 (m, 8H), 3.81 (s, 2H), 3.96 (s, 3H), 4.59 (s, 2H), 4.40 (s, 4H), 7.45 (s, 1H), 7.65 (s, 1H).

Elemental analysis: Calculated for $C_{19}H_{22}ClN_3O_4$: C 58.24, H 5.66, N 10.72. Found: C 58.08, H 5.72, N 10.63.

Example 13e

[7-chloro-9-(4-methyl-piperazin-1-yl-methyl)-2,3-dihydro-[1,4]dioxino[2,3-g]quinolin-8-yl]-methanol A 4-necked 5-L round-bottom flask is equipped with an overhead mechanical stirrer, a water-cooled condenser and nitrogen flow is maintained. The flask is charged with [7-chloro-9-(4-methyl-piperazin-1-yl-methyl)-2,3-dihydro [1,4]dioxino[2,3-g]quinoline-8-carboxylic acid methyl ester (194 g, 495 mol), prepared as in example 13d, as a solution in 1 L of methylene chloride. To the solution is added 1M diisobutylaluminum hydride in methylene chloride (2.00 L, 2.00 mol) over 15 min. The solution is heated to reflux during the addition. The reaction is allowed to cool to ambient temperature and stirred for 4 h. The reaction mixture is transferred to a 15-L separatory funnel containing a saturated solution of Rochelle's salt (5 L). After being stirred for 2.5 h, the organic layer is separated and the aqueous layer is extracted with methylene chloride (3×2.5 L). The combined organic layers are washed with brine (3 L), dried over anhydrous sodium sulfate and concentrated in vacuo. The resultant thick brown slurry is successively treated with methylene chloride (500 mL) and hexane (1 L). The mixture is swirled at 0° C. for 30 min. The precipitate is collected on a Büchner funnel, washed with 1 liter of hexane and dried in vacuo. at 30° C. yielding [7-chloro-9-(4-methyl-piperazin-1-ylmethyl)-2,3-dihydro-[1,4]dioxino[2,3-g] quinolin-8-yl]-methanol as a yellow crystalline solid: mp 178°–180° C. $^1$H NMR (CDCl$_3$, 200 MHz) δ2.26 (s, 3H), 2.63 (br. s, 4H), 4.00 (s, 2H). 4.39(s, 4H), 4.93 (s, 2H), 6.10 (br. s, 1H), 7.46 (s, 1H), 7.51 (s, 1H). Elemental analysis: Calculated for $C_{18}H_{22}ClN_3O_3$: C 59.42, H 6.09, N 11.55. Found: C 59.41, H 6.12, N 11.46.

Example 13f 7-chloro-9-(4-methyl-piperazin-1-yl-methyl)-2,3-dihydro-[1,4]dioxino[2,3-g]quinolin-8-carbaldehyde A 3-necked 4-L round-bottom flask is equipped with a mechanical stirrer and a 250-mL addition funnel. Under nitrogen, the flask is charged with methylene chloride (800 mL), followed by addition of oxalyl chloride (28.8 mL, 330 mmol). The solution is cooled to −78° C. and dimethyl sulfoxide (46.7 mL, 660 mmol) is added over 6 min. The temperature of the solution increases to −58° C. during the addition and is cooled back to about −70° C. After stirring for 3 min, [7-chloro-9-(4-methyl-piperazin-1-yl-methyl)-2,3-dihydro-[1,4]dioxino[2,3-g]quinolin-8-yl]-methanol (100 g, 275 mmol), prepared as in example 13e, is added as a solution in 140 mL of methylene chloride over 10 min. The yellow slurry is stirred for 45 min, then anhydrous triethylamine (153 mL, 1.10 mol) is added over 4 min. Stirring is continued for 10 min at −78° C., then the cooling bath is removed. The reaction mixture is allowed to warm to −5° C. and poured into 2 L of water. The organic layer is separated and the aqueous layer is extracted with methylene chloride (3×1.5 L). The combined organic layers are washed with brine (2 L), dried over anhydrous sodium sulfate and concentrated in vacuo yielding 7-chloro-9-(4-methyl-piperazin-1-ylmethyl)-2,3-dihydro-[1,4]dioxino[2,3-g]quinolin-8-carbaldehyde as a dark solid. This crude product is used for the next step without further purification. Recrystallization from $CH_2Cl_2$—MeOH (5:1) provided an analytical sample as a light yellow solid:140°–142° C. (dec.). $^1$H NMR (CDCl$_3$, 200 MHz) δ2.30 (s, 3H), 2.45, 2.59 (m, 8H), 3.98 (s, 2H). 4.41(s, 4H), 7.46 (s, 1H), 7.53 (s, 1H), 10.4 (s, 1H). Elemental analysis: Calculated for C$_{18}$H$_{20}$ClN$_3$O$_3$: C 59.75, H 5.57, N 11.61. Found: C 59.78, H 5.62, N 11.64.

Example 13g 7-iodo-9-(4-methyl-piperazin-1-yl-methyl)-2,3-dihydro-[1,4]dioxino[2,3-g]quinolin-8-carbaldehyde A 4-necked 12-L round-bottom flask is equipped with a mechanical stirrer and water-cooled condenser. Under nitrogen, the flask is charged with 7-chloro-9-(4-methyl-piperazin-1-yl-methyl)-2,3-dihydro-[1,4]dioxino[2,3-g] quinolin-8-carbaldehyde (120 g, 346 mmol), prepared as in example 13f, sodium iodide (1.04 kg, 6.92 mmol), and 3 L of acetonitrile. To the yellow suspension is added concentrated hydrogen chloride (59.7 mL, 726 mmol) over 5 min. The white slurry is refluxed for 15 hr. The solvent is mostly removed by short-path distillation in vacuo. The resultant thick slurry is cooled to ambient temperature and treated with 2.5 L of water and 2.5 L of methylene chloride. The organic layer is separated and the aqueous layer is extracted with methylene chloride (3×2 L). The combined organic layers are washed with brine (2.5 L), dried over anhydrous sodium sulfate, concentrated and dried in vacuo at 30° C. yielding 7-iodo-9-(4-methyl-piperazin-1-yl-methyl)-2,3-dihydro-[1,4]dioxino[2,3-g]quinolin-8-carbaldehyde as a yellow solid. This crude product is used for the next step without further purification. Recrystallization from CH$_2$Cl$_2$—MeOH (1:1) gave an analytical sample as an off-white solid: 198°–200° C. (dec.). $^1$H NMR (CDCl$_3$, 200 MHz) δ2.30 (s, 3H), 2.43, 2.57 (m, 8H), 3.93 (s, 2H). 4.40(s, 4H), 7.47 (s, 1H), 7.50 (s, 1H), 10.1 (s, 1H). Elemental analysis: Calculated for C$_{18}$H$_{20}$IN$_3$O$_3$: C 47.70, H 4.45, N 9.27. Found: C 47.78, H 4.45, N 9.26.

Example 13h

[7-iodo-9-(4-methyl-piperazin-1-yl-methyl)-2,3-dihydro-[1,4]dioxino[2,3-g]quinolin-8-yl]-methanol A 3-necked 2-L round-bottom flask is equipped with an overhead mechanical stirrer and nitrogen flow is maintained. The flask is charged with 7-iodo-9-(4-methyl-piperazin-1-ylmethyl)-2,3-dihydro-[1,4]dioxino[2,3-g]quinolin-8-carbaldehyde (105 g, 232 mmol), prepared as in example 13g, as a suspension in 700 mL of methanol. The mixture is cooled to 0° C., then sodium borohydride (8.76 mmol) is added in three portions over 15 min. The mixture is allowed to warm to ambient temperature and stirred for 2 hr. The solvent is mostly removed in vacuo and the resultant residue is treated with 2.5 L of water and extracted with methylene chloride (4×1.5 L). The combined organic layers are washed with brine (2.5 L), dried over anhydrous sodium sulfate, filtered, and concentrated in vacuo. The resultant solid residue is successively treated with 300 mL of methylene chloride and 300 mL of MeOH-EtOAc (1:1). The mixture was swirled at 0° C. for 30 min. The precipitate is filtered by suction, washed with 500 mL of hexane and dried in vacuo at 30° C. yielding [7-iodo-9-(4-methyl-piperazin-1-ylmethyl)-2,3-dihydro-[1,4]dioxino[2,3-g]quinolin-8-yl]-methanol as an off-white powder: mp 201°–203° C. (dec.). $^1$H NMR (CDCl$_3$, 200 MHz): δ2.26 (s, 3H), 2.62 (m, 8H), 4.02 (s, 2H). 4.39(s, 4H), 4.93 (m, 2H), 6.05 (br. s, 1H), 7.49 (s, 1H), 7.51 (s, 1H). HRMS (EI+): Calculated for C$_{18}$H$_{22}$N$_3$O$_3$: 455.0706. Found: 455.0699.

Example 13i

4(S)-4-ethyl-4-hydroxy-4,7-dihydro-1H-pyrano[3,4-c]pyridin-3,8-dione

A 1-liter 3-necked round bottom flask is equipped with an overhead mechanical stirrer and a condenser, under nitrogen, the flask is charged with 1N hydrochloric acid (600 mL) and 101 g of crude 4(S)-4-ethyl-4-hydroxy-8-methoxy-1,4-dihydro-pyrano[3,4-c]pyridin-3-one prepared as in example 3. The resulting solution is heated at reflux for 14 hr. The reaction mixture is cooled to ambient temperature and then concentrated to a solid. The solids are recrystallized in methanol (75 mL) yielding 4(S)-4-ethyl-4-hydroxy-4,7-dihydro-1H-pyrano[3,4-c]pyridin-3,8-dione. mp 224°–226° C.; $^1$H-NMR (400 MHz, DMSO-d6) δ11.85 (s, 1H), 7.44 (d, J=7 Hz, 1H), 6.36 (d, J=7 Hz, 1H), 6.28 (s, 1H), 5.24 (s, 2H), 3.36 (s, 3H), 2.99 (s, 1H), 1.75 (m, 2H), 0.81 (t, J=7 Hz, 3H); Calculated for C10H11NO4; C 57.4%, H 5.30%, N 6.70%: Found; C 56.59%, H 5.26%, N 6.66%; MS (EI) 209 (M+); [a]D$^{22}$ +115.4° [c 0.877, MeOH]; Optical purity determined by chiral HPLC: 10% ethanol/hexane, 26° C., 1 mL/min., l=300 nm, Chiralcel-OD column 250×4.6 mm. i.d.

Example 13j

4(S)-4-ethyl-4-hydroxy-7-[7-iodo-9-(4-methyl-piperazin-1-yl-methyl)-2,3-dihydro-[1,4]dioxino[2,3-g]quinolin-8-yl-methyl]4,7-dihydro-1H-pyrano[3,4-c]pyridine-3,8-dione A 4-necked 2-L round-bottom flask is equipped with mechanical stirrer, and water cooled condenser. Under nitrogen, the flask is charged with 4(S)-4-ethyl-4-hydroxy-4,7-dihydro-1H-pyrano[3,4-c]pyridin-3,8-dione (26.7 g, 128 mmol), prepared as in example 13i, [7-iodo-9-(4-methyl-piperazin-1-yl-methyl)-2,3-dihydro-[1,4]dioxino[2,3-g]quinolin-8-yl]-methanol (58.1 g, 128 mmol), as prepared in example 13h, triphenylphosphine (33.5 g, 128 mmol) and 318 mL of methylene chloride. The suspension is stirred for 15 min, then diethyl azodicarboxylate (20.1 mL, 128 mmol) is added dropwise over 15 min. During the addition, gentle reflux of the solvent is observed. The brown solution is allowed to cool to ambient temperature and stirred for 6.5 h. The solvent is removed in vacuo. and the resulting residue is treated with 400 mL of benzene and swirled for 3 min. The formed precipitate is filtered by suction and washed with 50 mL of cold benzene. The filtrate is concentrated and the resultant solid is chromatographed on silica gel. Elution with 3–50% MeOH in CHCl$_3$ affords a light yellow solid, which is dissolved in 500 mL MeOH/CH$_2$Cl$_2$ (1:100). Recrystallization is then initiated by addition of ethyl acetate and filtration by suction and drying in vacuo. The filtrate from the recrystallization is partially concentrated and a second recrystallization is performed. A third recrystallization in the same fashion yields 4(S)-4-ethyl-4-hydroxy-7-[7-iodo-9-(4-methyl-piperazin-1-yl-methyl)-2,3-dihydro-[1,4]dioxino[2,3-g]quinolin-8-yl-methyl]-4,7-dihydro-1H-pyrano[3,4-c]pyridine-3,8-dione slightly contaminated with ethyl acetate: mp 158°–163° C. (dec.). [α]$_D$=+1.9° (MeOH, c 1.29). $^1$H NMR (CDCl$_3$, 200 MHz) δ0.98 (t, J=7.3 Hz, 3H), 1.83 (q, J=7.3 Hz, 2H), 2.19 (s, 3H), 2.15–2.49 (m, 9H), 3.54 (m, 2H), 4.42 (m, 4H), 5.46 (ABq, J$_{AB}$=15.4 Hz, Δv=94.4 Hz, 2H), 5.51 (ABq, J$_{AB}$=16.3 Hz, Δv=110, Hz, 2H), 6.48 (d, J=7.2 Hz, 1H), 7.20 (d, J=7.2 Hz, 1H), 7.38 (s, 1H), 7.40 (s, 1H). HRMS (EI+): Calculated for C$_{28}$H$_{31}$IN$_4$O$_6$: 46.1239 Found: 646.1304.

Example 13k 7-(4-methylpiperazinomethylene)-10,11-ethylenedioxy-20(S)-camptothecin A 4-necked 3-L round bottom flask is equipped with mechanical stirrer, and water-cooled condenser. Under nitrogen, the flask is charged with 4(S)-4-ethyl-4-hydroxy- 7-[7-iodo-9-(4-methyl-piperazin-1-yl-methyl)-2,3-dihydro-[1,4]dioxino[2,3-g]quinolin-8-yl-methyl]-4,7-dihydro-1H-pyrano[3,4-c]pyridine-3,8-dione (30.0 g, 46.4 mmol), prepared as in example 13j, palladium(II) acetate (213 mg, 0.928 mmol), anhydrous potassium carbonate powder (12.8 g, 92.8 mmol), triphenylphosphine (6.09 g, 23.2 mmol) and anhydrous acetonitrile (1.8 L). The suspension is brought to reflux during which time the solids dissolve. As the reflux is continued for 16 h, the product precipitates. The reaction mixture is cooled to 0° C. and stirred for an additional 2.5 h. The precipitate is collected on a Fritted funnel and the resulting yellow cake is treated with 1 L of chloroform. The suspension is filtered and washed with chloform (5×200 mL), the combined filtrates are concentrated to 300 mL and treated with 30.0 g of triphenylphosphine. After being stirred at ambient temperature for 30 min, the solution is treated with 100 mL of acetone. The resulting precipitate is filtered by suction yields 7-(4-methylpiperazinomethylene)-10,11-ethylenedioxy-20(S)-camptothecin as a light yellow powder. The product is further purified by stirring as a solution in 220 mL of MeOH/CHCl$_3$ (1:10) containing 5.6 g of triphenylphosphine, followed by precipitation with 50 mL of acetone. The precipitate is collected on a Büchner funnel and dried in vacuo. At this stage, analysis shows palladium and phosphorus. Further purification is carried out by dissolving the compound in 165 mL of MeOH/CHCl$_3$ (1:10), followed by precipitation with 150 mL of acetone; filtration and drying in vacuo at ambient temperature. Analysis indicated nondetectable amount (<2 ppm) of palladium and phosphorus in the product: mp: 275° C. (dec.). [α]$_D$=+22.6° (CHCl$_3$, c 1.02). $^1$H NMR (CDCl$_3$, 400 MHz); δ1.04 (t, J=7.4 Hz, 3H), 1.87 (m, 2H), 2.31 (s, 3H), 2.20–2.59 (m, 9H), 3.97 (s, 2H) 4.46 (s, 4H), 5.32 (s, 2H), 5.55 (ABq, J$_{AB}$=16.2 Hz, Δν=180 Hz, 2H), 7.60 (s, 1H), 7.66 (s, 1H), 7.72 (s, 1H). Elemental analysis: Calculated for C$_{28}$H$_{30}$N$_4$O$_6$: C 64.85, H 5.83, N 10.80. Found: C 64.34, H 5.83, N 10.71.

Example 13l 7-(4-methylpiperazinomethylene)-10,11-ethylenedioxy-20(S)-camptothecin dihydrochloride A four-necked 1-L round-bottom flask is equipped with a mechanical stirrer and water cooled condenser. Under nitrogen, the flask is charged with free base 7-(4-methylpiperazinomethylene)-10,11-ethylenedioxy-20(S)-camptothecin (14.0 g, 27.0 mmol), prepared as in example 13k, and 350 mL of 6N HCl. The suspension is brought to reflux for 35 min. A small amount of precipitate is generated after initial complete solution formation. Without being cooled, the mixture is filtered through a Supor (0.45 m) filtering membrane. Washing with hot 6N HCl (100 mL) dissolves the above precipitate. The combined filtrates are cooled to 35° C. Recrystallization is initiated by addition of 20 mL of 200 proof ethanol. After stirring for 1 h, 150 mL more ethanol is added. The mixture is allowed to stand at 0° C. for 24 h. Filtration and drying in vacuo. at 70° C. yields 7-(4-methylpiperazinomethylene)-10,11-ethylenedioxy-20 (S)-camptothecin dihydrochloride as a yellow powder. A $^1$H NMR shift study with Eu(hfc)$_3$ indicates a single enantiomer. mp 280° C. (dec.). [α]$_D$=–6.72° (H$_2$O, c 0.67). $^1$H NMR (D$_2$O, 400 MHz) δ0.92(t, J=7.2 Hz, 3H), 1.89 (m, 2H), 2.55 (m, 2H), 2.81 (s, 3H), 2.96 (m, 2H), 3.11 (m, 2H), 3.41 (m, 3H), 3.71 (s, 2H), 5.32 (ABq, J$_{AB}$=16.1 Hz, Δν=2H), 6.84 (s, 1H), 6.97 (s, 1H), 7.00 (s, 1H). Elemental analysis: Calculated for C$_{28}$H$_{30}$N$_4$O$_6$.2HCl.H$_2$O: C 55.18, H 5.62, N 9.19, Cl 11.63. Found: C 55.41, H 5.70, N 9.24, Cl 11.52.

Example 14

7-chloro-9-(4-methylpiperazin-1-ylmethyl)-2,3-dihydro[1,4]dioxino[2,3-g]quinoline-8-carboxylic acid methyl ester A 4-necked 5-L round-bottom flask is equipped with a mechanical stirrer and 250-mL addition funnel. Under nitrogen, the flask is charged with 7-chloro-9-chloromethyl-2,3-dihydro[1,4]dioxino[2,3-g]quinoline-8-carboxylic acid methyl ester, prepared as in example 13c (6, 340 g, 1.04 mol), and methylene chloride (2 L). To the stirred solution is added N-methylpiperazine (237 mL, 2.14 mol) over 10 min. After the addition is complete, the reaction mixture is stirred at ambient temperature for 15 h. The reaction mixture is poured into water (3 L) and the organic layer is separated. The aqueous layer is extracted with methylene chloride (3×2 L). The combined organic layers are washed with brine (2 L), dried over anhydrous sodium sulfate and concentrated in vacuo The resultant thick brown slurry is successively treated with methylene chloride (300 mL) and hexane (1.5 L). The mixture is swirled at 0° C. for 30 min. The precipitate is collected on a Büchner funnel, washed with hexane (1 L) and dried in vacuo. at 30° C. yielding 7-chloro-9-(4-methylpiperazin-1-ylmethyl)-2,3-dihydro[1,4]dioxino [2,3-g]quinoline-8-carboxylic acid methyl ester as a yellow powder: mp 143° C. $^1$H NMR (CDCl$_3$, 200 MHz) d 2.28 (s, 3H), 2.38–2.49 (m, 8H), 3.81 (s, 2H), 3.96 (s, 3H), 4.59 (s, 2H), 4.40 (s, 4H), 7.45 (s, 1H), 7.65 (s, 1H). Elemental analysis: Calculated for C$_{19}$H$_{22}$ClN$_3$O$_4$: C 58.24, H 5.66, N 10.72. Found: C 58.08, H 5.72, N 10.63.

Example 15

1-(7-amino-2,3-dihydro-benzo[1,4]dioxin-6-yl)-2-chloro-ethanone 1,4-benzodioxan-6-amine, available from the Aldrich Chemical Company, Inc., 1001 West Saint Paul Avenue, Milwaukee, Wis. 53233, (160 g, 1.06 mol) is dissolved in dichloromethane (2.4 L) and cooled in an ice bath to less than 10° C. Boron trichloride gas (150 g, 1.27 mol, 1.2 eq) is added over 0.75 hour. The resulting brown slurry is then stirred overnight at room temperature. The slurry is then cooled in an ice bath to 10° C. and chloroacetonitrile (94 mL, 1.48 mol, 1.4 eq) is added in one portion. Gallium chloride (205 g, 1.16 mol, 1.1 eq) is dissolved in dichloromethane (310 mL) and added to the reaction over 0.5 h. The resulting brown slurry is then heated at reflux overnight (13–24 h). The brown solution is then cooled to rt and poured into a stirred mixture of dichloromethane (6.4 L)) and water (6.4 L). The mixture is stirred for 1.5 to 2 h to allow the solids to dissolve. The layers are then separated and the aqueous phase is extracted with dichloromethane (2 L). The organic layers are combined and concentrated under vacuum (about 100 mm Hg) to about 320 mL. (Crystallization occurs during the concentration.) Heptane (640 mL) is added over 1 hour and the slurry stirred overnight at room temperature. The slurry is filtered, washing the cake with heptane (200 mL). The cake is then dried overnight at 40° C. under high vacuum (about 1 mm Hg) to give 206 g (86%) of 1-(7-amino-2,3-dihydro-benzo[1,4] dioxin-6-yl)-2-chloro-ethanone as a yellow solid.

Example 16

9-chloromethyl-7-oxo-2,3,6,7-tetrahydro[1,4]dioxino [2,3-g]quinoline-8-carboxylic acid ethyl ester To a mixture of 1-(7-amino-2,3-dihydro-benzo[1,4] dioxin-6-yl)-2-chloro-ethanone (230 g. 1.01 mol) prepared as in example 15, in acetonitrile (1.5 L) and triethylamine (197 mL, 1.41 mol, 1.4 eq) is added ethyl malonyl chloride (180 mL, 1.41 mol, 1.4 eq) over 0.5 h while keeping the reaction temperature less than 30° C. with an ice bath. After the addition is complete the reaction is stirred 1.5 h at room temperature. A second charge of triethylamine (140 mL, 1.01 mol, 1.0 eq) is added and the reaction is stirred for 4.5 hours. Water (2.1 L) is added slowly followed by conc. HCl (115 mL). The slurry is stirred overnight at rt, filtered, and the solid washed with water (460 mL). The solid is then dried under high vacuum (about 1 mm Hg) at 40° C. to yield 9-chloromethyl-7-oxo-2,3,6,7-tetrahydro[1,4]dioxino[2,3-g]quinoline-8-carboxylic acid ethyl ester as a yellow solid. HRMS (EI$^+$): calc for $C_{15}H_{14}NO_5Cl$: 323.0561, Found: 323.0556.

Example 17

7-bromo-9-bromomethyl-2,3-dihydro[1,4]dioxino[2,3-g]quinoline-8-carboxylic acid ethyl ester hydrobromic acid salt To a mixture of 9-chloromethyl-7-oxo-2,3,6,7-tetrahydro[1,4]dioxino[2,3-g]quinoline-8-carboxylic acid ethyl ester (25 g, 0.077 mol), prepared as in example 16, in 1,2-dichloroethane (DCE, 90 mL) is added a solution of phosphorus oxybromide (44 g, 2 eq) in DCE (90 mL). The resultant mixture is heated at reflux for about 4.0 h, and then cooled to <15° C. Ethanol (91 mL, 20.0 eq) is added while keeping the temp <20° C. The mixture is then allowed to warm to room temperature and stirred overnight. The mixture is filtered and the solid is washed with DCE (30 mL). The solid is dried under high vacuum (about 1 mm Hg) at room temperature overnight to yield 7-bromo-9-bromomethyl-2,3-dihydro[1,4]dioxino[2,3-g]quinoline-8-carboxylic acid ethyl ester hydrobromic acid salt as a yellow solid. MP (207° C. (dec.)), HRMS (EI$^+$): calc for $C_{15}H_{13}NO_4Br_2$ (free base): 428.9211, Found: 428.9238.

Example 18

[7-bromo-9-(4-methylpiperazin-1-yl-methyl)-2,3-dihydro-[1,4]dioxino[2,3-g]quinolin-8-yl]-methanol To a mixture of 7-bromo-9-bromomethyl-2,3-dihydro[1,4]dioxino[2,3-g]quinoline-8-carboxylic acid ethyl ester hydrobromic acid salt, prepared as in example 17 (10 g, 19.6 mmol) in dichloromethane (100 mL) is added triethylamine (5.4 mL. 39.2 mmol) followed by N-methylpiperazine (2.79 mL, 25.5 mmol). After stirring 30 min, water (50 mL) is added and the mixture is stirred 10 min. The layers are separated and the aqueous phase is extracted with dichloromethane (50 mL). The organic phases are combined and washed with water (2×50 mL). The organic solution is then concentrated to an oil. The oil is diluted with dichloromethane (50 mL) and stirred while diisobutylaluminum hydride (1.0M in dichloromethane, 53 mL. 53 mmol) is added slowly while keeping the reaction temperature below 30° C. using an ice bath. The reaction is stirred for 10 min and then slowly poured into an aqueous solution (75 mL) saturated with potassium sodium tartrate tetrahydrate (Rochelle's salt). The temperature is kept <30° C. with an ice bath during the addition. The mixture gels and is stirred overnight at room temperature. The layers are separated and the aqueous phase is extracted with dichloromethane (2×75 mL). The organics are combined and washed with water (2×50 mL). The organic phase is then concentrated under vacuum (crystallization occurs during concentration) to about 20 mL and the rest of the product crystallized out by adding tert-butyl methyl ether. The slurry is filtered and dried on high vacuum at room temperature overnight to provide 6.87 g (86%) of [7-bromo-9-(4-methyl-piperazin-1-ylmethyl)-2,3-dihydro-[1,4]dioxino[2,3-g]quinolin-8-yl]-methanol as a tan solid. MP (184°–186° C.), HRMS calc for $C_{18}H_{22}N_3O_3Br$: 407.0841, Found: 407.0827.

Example 19

4(S)-4-ethyl-4-hydroxy-4,7-dihydro-1H-pyrano[3,4-c]pyridin-3,8-dione

A mixture of 4(S)-4-ethyl-4-hydroxy-8-methoxy-1,4-dihydro-pyrano[3,4-c]pyridin-3-one (30.3 g crude material) prepared as in example 7 and 1N hydrochloric acid (120 mL) is heated at 90°–95° C. for about 2 h. The solution is filtered while hot through a course glass frit, and the resultant filtrate stirred while cooling to generate a precipitate. The crystals were collected by filtration and washed with tert-butyl methyl ether (2×15 mL) and air-dried for 2 h to yield 9.28 g of 4(S)-4-ethyl-4-hydroxy-4,7-dihydro-1H-pyrano[3,4-c]pyridin-3,8-dione as a yellow-brown solid.

Example 20

4(S)-4-ethyl-4-hydroxy-7-[7-bromo-9-(4-methylpiperazin-1-yl-methyl)-2,3-dihydro-[1,4]dioxino[2,3-g]quinolin-8-yl-methyl]-4,7-dihydro-1H-pyrano[3,4-c]pyridine-3,8-dione To a mixture of 4(S)-4-ethyl-4-hydroxy-4,7-dihydro-1H-pyrano[3,4-c]pyridin-3,8-dione, prepared as in example 19 (240 g, 1.15 moles), [7-bromo-9-(4-methyl-piperazin-1-yl-methyl)-2,3-dihydro-[1,4]dioxino[2,3-g]quinolin-8-yl]-methanol, prepared as in example 18 (609 g, 1.49 moles), and triphenylphosphine (361 g, 1.38 moles) in 2.0 liters of dichloromethane is added diethylazodicarboxylate (217 ml, 1.38 moles). The reaction warms to reflux during the addition. After the addition is complete, the mixture is stirred for 50 minutes. The mixture is filtered to remove any solids. To the filtrate is added tert-butyl methyl ether (3.1 liters) with stirring, causing a precipitate to form. The resultant mixture is cooled to about 1° C., filtered, and washed with tert-butyl methyl ether. The solid is mixed with 2.9 liters of dichloromethane and 100 mL of methanol, stirred for 15 minutes and filtered. To the filtrate is added with stirring tert-butyl methyl ether (5 L), causing a precipitate to form. The mixture is cooled to 3° C., the solid is collected by filtration, and rinsed with tert-butyl methyl ether. After vacuum drying the solid, obtained 492 g (71%) of 4(S)-4-ethyl-4-hydroxy-7-[7-bromo-9-(4-methyl-piperazin-1-yl-methyl)-2,3-dihydro-[1,4]dioxino[2,3-g]quinolin-8-yl-methyl]-4,7-dihydro-1H-pyrano[3,4-c]pyridine-3,8-dione. MP (183°–188° C. (dec.)). HRMS (EI$^+$): calc for $C_{28}H_{31}BrN_4O_6$: 589.1427, Found: 589.1441.

Example 21

7-(4-methylpiperazinomethylene)-10,11-ethylenedioxy-20(S)-camptothecin

After purging with nitrogen, 4(S)-4-ethyl-4-hydroxy-7-[7-bromo-9-(4-methyl-piperazin-1-yl-methyl)-2,3-dihydro-[1,4]dioxino[2,3-g]quinolin-8-yl-methyl]-4,7-dihydro-1H-pyrano[3,4-c]pyridine-3,8-dione (216 g, 0.36 mol) prepared as in example 20, palladium(II) acetate (4.85 g, 0.0216 mol), powdered potassium carbonate (74.6 g, 0.54 mol), and triphenylphosphine (47.2 g, 0.18 mol) in acetonitrile (9 L) are refluxed under nitrogen for about 12 hours. The mixture is cooled to about 0° C., filtered, and rinsed with acetonitrile (0.2 L). The crude solid is mixed with dichloromethane (3.25 L) and methanol (550 mL), stirred for about 0.5 hours, filtered, and washed with dichloromethane (0.2 L). The filtrate is treated with triphenylphosphine (54 g) and stirred under nitrogen for about 1.5 hours. Acetone (1.9 L) is added (65 ml/min) with stirring, causing a precipitate to form. The mixture is cooled at 0° C. for 4 hours. The mixture is filtered, and the solid is washed with acetone (0.2 L), and air-dried to give crude product (146 g, 78%). The crude product is dissolved in dichloromethane (2.5 L) and methanol (0.3 L) for 0.5 hours. Triphenylphosphine (36.5 g, 0.39 equiv) is added and the solution is stirred at RT for 2.5 hours under nitrogen. Acetone (1.7 L) is added (85 ml/min) causing a precipitate to form. The resulting mixture is cooled at 0° C. for 4 hours. Filtration, washing with acetone (0.4 L), and drying at 30° C. provides crude product (135 g, 72%). The product is dissolved in dichloromethane (2 L) and methanol (0.31 L). Acetone (1.6 L) is added dropwise to the solution causing a precipitate to form. The slurry is cooled at 0° C. for 4 hours. Filtration, washing with acetone (0.2 L), and drying at 30° C. provides crude product (124.8 g, 67%). The crude product is dissolved in dichloromethane (1.6 L) and methanol (350 mL). Acetone (1.4 L) is added (280 ml/min) causing a precipitate to form. The slurry is cooled at 0° C. for 3.5 hours. Filtration, washing with acetone (0.25 vol/wt), and vacuum-drying at 40° C. provides 115 g (61%) of 7-(4-methylpiperazinomethylene)-10,11-ethylenedioxy-20 (S)-camptothecin as a yellow solid.

What is claimed is:

1. A method of removing Group VIII heavy metal contamination from an organic composition wherein said organic composition is a mixture of an organic compound and a Group VIII heavy metal contaminant comprising the steps of:

i) dissolving the organic composition in one or more suitable first solvents forming a solution;

ii) treating the solution with a ligand soluble in the solution; and iii) precipitating the organic compound with one or more suitable second solvents.

2. The method of claim 1 wherein the heavy metal contaminant is selected from the group consisting of: palladium, osmium, iron, cobalt, rhodium, nickel, and platinum.

3. The method of claim 1 wherein the heavy metal contaminant is palladium.

4. The method of claim 2 wherein the first solvent is selected from the group consisting of: polar-aprotic and polar-protic solvents.

5. The method of claim 3 wherein the the ligand is selected from the group consisting of: triarylphosphines, trialkylphosphines.

6. The method of claim 4 wherein the second solvent is selected from the group consisting of: polar-aprotic and non-polar-aprotic solvents.

7. The method of claim 5 wherein the organic composition is a mixture of a camptothecin analog and a Group VIII heavy metal contaminant.

* * * * *